(12) United States Patent
Edge et al.

(10) Patent No.: US 12,427,128 B2
(45) Date of Patent: Sep. 30, 2025

(54) SENSORINEURAL HAIR CELL DIFFERENTIATION

(71) Applicant: Massachusetts Eye and Ear Infirmary, Boston, MA (US)

(72) Inventors: Albert Edge, Brookline, MA (US); Judith Kempfle, Brookline, MA (US); Dunia Abdul-Aziz, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 676 days.

(21) Appl. No.: 17/708,927

(22) Filed: Mar. 30, 2022

(65) Prior Publication Data

US 2022/0218638 A1    Jul. 14, 2022

Related U.S. Application Data

(60) Division of application No. 16/813,668, filed on Mar. 9, 2020, now Pat. No. 11,298,328, which is a continuation of application No. 15/306,657, filed as application No. PCT/US2015/028035 on Apr. 28, 2015, now Pat. No. 10,603,295.

(60) Provisional application No. 61/985,170, filed on Apr. 28, 2014.

(51) Int. Cl.
| | | |
|---|---|---|
| *A61K 31/19* | (2006.01) | |
| *A61K 9/00* | (2006.01) | |
| *A61K 31/137* | (2006.01) | |
| *A61K 31/165* | (2006.01) | |
| *A61K 31/7088* | (2006.01) | |
| *A61K 38/12* | (2006.01) | |
| *A61K 38/17* | (2006.01) | |
| *A61K 45/06* | (2006.01) | |
| *A61P 27/16* | (2006.01) | |

(52) U.S. Cl.
CPC ............ *A61K 31/19* (2013.01); *A61K 9/0019* (2013.01); *A61K 9/0046* (2013.01); *A61K 31/137* (2013.01); *A61K 31/165* (2013.01); *A61K 31/7088* (2013.01); *A61K 38/12* (2013.01); *A61K 38/1709* (2013.01); *A61K 45/06* (2013.01); *A61P 27/16* (2018.01)

(58) Field of Classification Search
CPC .............................. A61P 27/16; A61K 9/0046
See application file for complete search history.

(56) References Cited

U.S. PATENT DOCUMENTS

| 7,541,431 | B2 | 6/2009 | Yoon |
| 2005/0130145 | A1 | 6/2005 | Yue et al. |
| 2006/0264897 | A1 | 11/2006 | Lobl et al. |
| 2007/0059829 | A1 | 3/2007 | Yoon |
| 2007/0185049 | A1 | 8/2007 | Jadhav et al. |
| 2009/0076160 | A1 | 3/2009 | Lendvai et al. |
| 2011/0245235 | A1 | 10/2011 | Hanley |
| 2012/0207744 | A1 | 8/2012 | Mendlein et al. |
| 2013/0303555 | A1 | 11/2013 | Copeland et al. |

FOREIGN PATENT DOCUMENTS

| WO | WO 2010/060088 | 5/2010 |
| WO | WO 2012/005805 | 1/2012 |
| WO | WO 2012/087983 | 6/2012 |

OTHER PUBLICATIONS

Malik et al., "The role of DNA methylation in regulation of the murine Lhx3 gene," Gene 2014;534(2):272-81. PMID: 24183897. Available online Oct. 31, 2013. (Year: 2013).*
Bonfig et al., "A novel mutation of LHX3 is associated with combined pituitary hormone deficiency including ACTH deficiency, sensorineural hearing loss, and short neck—a case report and review of the literature," Eur. J. Pediatr. 2011;170(8):1017-21. PMID: 21249393. (Year: 2011).*
Bermingham et al., "Math1: an essential gene for the generation of inner ear hair cells," Science, 284(5421):1837-1841, 1999.
Blaha et al., "Does Monoamine Oxidase Inhibition by Pargyline Increase Extracellular Dopamine Concentrations In The Striatum?," Neuroscience, 1996, 75: 543-550.
Burton et al., The role of Pax2 in mouse inner ear development, Dev. Biol. 272: 161-175, 2004.
Doetzlhofer et al., "Hey2 regulation by FGF provides a Notch-independent mechanism for maintaining pillar cell fate in the organ of Corti," Dev. Cell, 16(1): 58-69, 2009.
Engelen et al., "Sox2 cooperates with Chd7 to regulate genes that are mutated in human syndromes," Nature Genetics, Jun. 2011, 43: 607-611.
Filipo et al., "Intratympanic prednisolone therapy for sudden sensorineural hearing loss: A new protocol," Acta Oto-Layngologica, 2010, 130:1209-1213.
Fleuren et al. "Prednisolone induces the Wnt signalling pathway in 3T3-L1 adipocytes," Arch Physiol Biochem, 2013, 119(2):52-64.
Gubbels et al., "Functional auditory hair cells produced in the mammalian cochlea by in utero gene transfer," Nature, 455(7212): 537-541, 2008.
Heikkila et al., "Prevention of MPTP-induced neurotoxicity by AGN-1133 and AGN-1135, selective inhibitors of monoamine oxidase-B," European Journal of Pharmacology, Oct. 1985, 116(3):313-317.
Hurd et al., "The ATP-dependent chromatin remodeling enzyme CHD7 regulates pro-neural gene expression and neurogenesis in the inner ear," Development, 2010, 137: 3139-3150.
International Preliminary Report on Patentability in International Application No. PCT/US 15/28035, mailed on Nov. 10, 2016, 8 pages.

(Continued)

*Primary Examiner* — Theodore R. Howell
(74) *Attorney, Agent, or Firm* — Fish & Richardson P.C.

(57) ABSTRACT

The present disclosure provides compositions and methods for treating subjects at risk for or with sensorineural hearing loss. Such compositions and methods include modulating the epigenetic status of the cell, or rate of protein degradation, to increase expression and/or levels of Atoh1 protein.

9 Claims, 12 Drawing Sheets

Specification includes a Sequence Listing.

(56) References Cited

OTHER PUBLICATIONS

International Search Report and Written Opinion in International Application No. PCT/US 15/28035, mailed on Nov. 2, 2015, 15 pages.
Izumikawa et al., "Auditory hair cell replacement and hearing improvement by Atoh1 gene therapy in deaf mammals," Nat. Med., 11: 271-276, 2005.
Jeon et al., "Notch signaling alters sensory or neuronal cell fate specification of inner ear stem cells," Neurosci., 31(23): 8351-8358, 2011.
Karytinos et al., "A Novel Mammalian Flavin-dependent Histone Demethylase," J. Biol. Chem, 2009, 18 pages.
Kelly et al., "Regulation of cell fate in the sensory epithelia of the inner ear," Nat. Rev. Neurosci., 7: 837-849, 2006.
Kiernan et al., "Sox2 is required for sensory organ development in the mammalian inner ear," Nature, 434(7036): 1031-1035, 2005.
Kim et al., "The Role of PTIP in Maintaining ES Cell Pluripotency," Stem Cell, Jul. 2009, 27: 1516-1523.
Kopp et al., "Small Increases in the Level of Sox2 Trigger the Differentiation of Mouse Embryonic Stem Cells," Stem Cells, 2008, 26: 903-911.
Lawoko-Kerali et al., "Expression of the transcription factors GATA3 and Pax2 during development of the mammalian inner ear," J. Comp. Neurol., 442(4): 378-391, 2002.
Marson et al., "Wnt signaling promotes reprogramming of somatic cells to pluripotency," Cell Stem Cell, Aug. 2008, 3: 132-135.
Martinez-Monedero et al., "Differentiation of inner ear stem cells to functional sensory neurons," Dev. Neurobiol., 68(5): 669-684, 2008.
Millimaki et al., "Sox2 is required for maintenance and regeneration, but not initial development, of hair cells in the zebrafish inner ear," Dev. Biol. 338(2): 262, 2010.
Moreno et al., "Characterization of new otic enhancers of the Pou3f4 gene reveal distinct signaling pathway regulation and spatiotemporal patters," PLoS One, 5(12): e15907, 2010.
Niwa and Umehara, "Structural insight into inhibitors of flavin adenine dinucleotide-dependent lysine demethylases," Epigenetics, 2017, 12: 340-352.
Ohyama et al., "Wnt signals mediate a fate decision between otic placode and epidermis," Development, 133: 865-875, 2006.
Pararas et al., "Microsystems technologies for drug delivery to the inner ear," Adv. Drug Deliv. Rev. 64(14):1650-60. PMID: 22386561. (Year: 2012).
Schimmenti et al., "Further delineation of renal-coloboma syndrome in patients with extreme variability of phenotype and identical PAX2 mutations," Am. J. Hum. Genet., 60: 869-878, 1997.
Shi et al., "Generation of hair cells in neonatal mice by B-catenin overexpression in Lgr5-positive cochlear progenitors," Proc. Natl. Acad. Sci. USA., 110(34): 13851-13856, 2013.
Torres et al., "Pax2 contributes to inner ear patterning and optic nerve trajectory," Development, 122: 3381-3391, 1996.
Warchol et al., "Expression of the Pax2 transcription factor is associated with vestibular phenotype in the avian inner ear," Dev. Neurobiol., 69(2-3): 191-202, 2009.
Yamamoto et al., "Inhibition of Notch/RBP-J signaling induces hair cell formation in neonate mouse cochleas," J. Mol. Med., 84(1): 37-45, 2006.
Yu et al., "Inhibition of H3K9 methyltransferases G9a/GLP prevents ototoxicity and ongoing hair cell death," Cell Death Dis, Feb. 2013, 4:e506.
Zeng et al., "Overexpression of Math1 induces robust production of extra hair cells in postnatal rat inner ears," Nat. Neurosci., 2000, 3(6): 580-586.

* cited by examiner

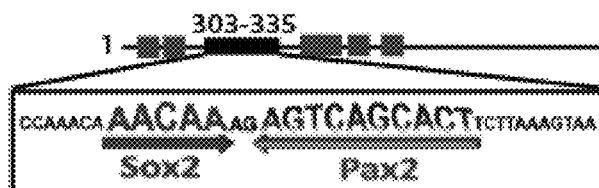
FIG. 1A
FIG. 1B
FIG. 2A
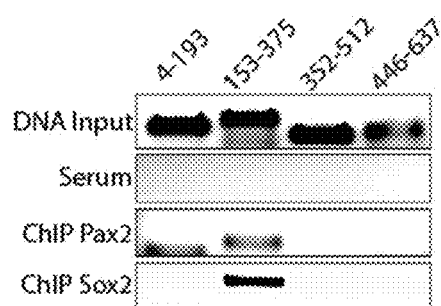
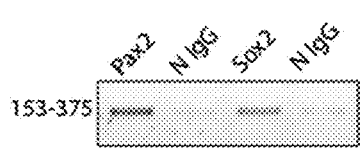
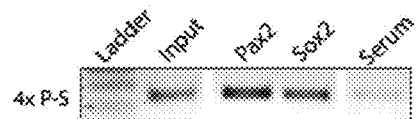
FIG. 2B  FIG. 2C
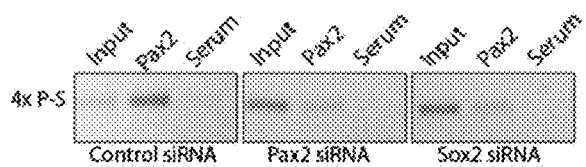
FIG. 2D

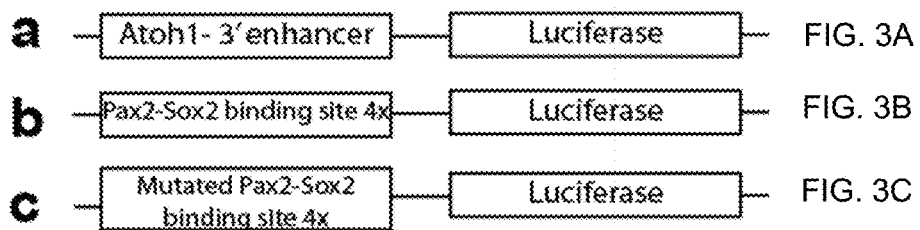
FIG. 3A
FIG. 3B
FIG. 3C
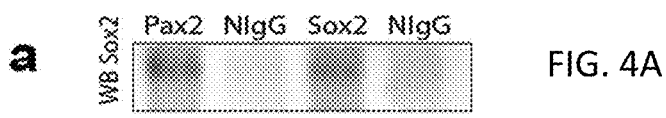
FIG. 4A
FIG. 4B
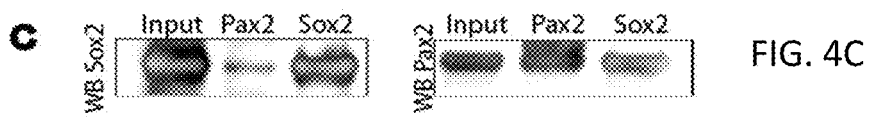
FIG. 4C

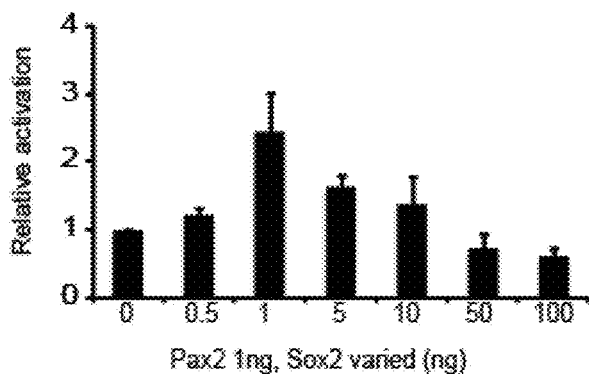
FIG. 7B
FIG. 8A
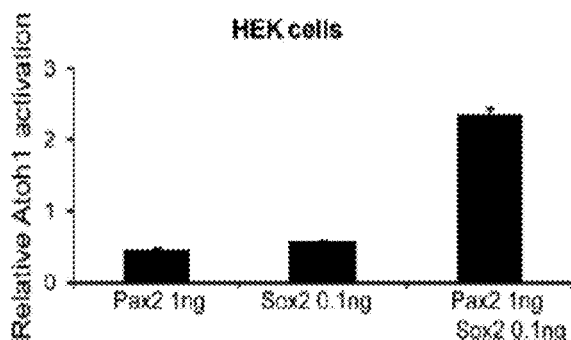 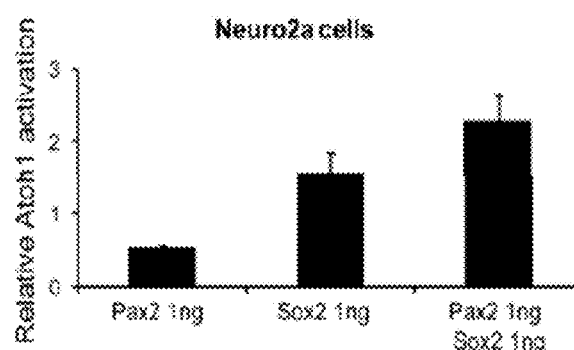
FIG. 8B  FIG. 8C

SENSORINEURAL HAIR CELL DIFFERENTIATION

CLAIM OF PRIORITY

This application is a divisional application of U.S. patent application Ser. No. 16/813,668, filed Mar. 9, 2020, which is a continuation application of U.S. patent application Ser. No. 15/306,657, filed Oct. 25, 2016, now U.S. Pat. No. 10,603,295, which is a 371 U.S. National Application of PCT/US2015/028035, filed on Apr. 28, 2015, which claims priority under 35 USC § 119(e) to U.S. Patent Application Ser. No. 61/985,170, filed on Apr. 28, 2014, the entire contents of which are hereby incorporated by reference.

This invention was made with government support under Grant Nos. DC005209, and DC007174 awarded by the National Institutes of Health. The government has certain rights in the invention.

SEQUENCE LISTING

This application contains a Sequence Listing that has been submitted electronically as an ASCII text file named "Sequence_Listing.txt." The ASCII text file, created on Mar. 28, 2022, is 5 kilobytes in size. The material the ASCII text file is hereby incorporated by reference in its entirety.

TECHNICAL FIELD

This invention relates to the generation of sensorineural hair cells, and more particularly to the use of epigenetic modulation of Atoh1 expression to generate sensorineural hair cells.

BACKGROUND

There are six distinct sensory organs in the mammalian inner ear: the three cristae of the semicircular canals, the two maculae of the saccule and utricle, and the organ of Corti of the cochlea. The organ of Corti is the organ of hearing. The receptor cell for hearing is the hair cell of the cochlea (referred to herein as a hair cell, a sensory hair cell, or a sensorineural hair cell). Hair cells are limited in number and do not regenerate in mammals; damage or death of these cells leads to hearing loss (Edge and Chen, Curr. Opin. Neurobiol., 18:377-382 (2008)). Therapeutic compositions and methods to increase sensorineural hair cell number and/or function in the cochlea are required to address hearing loss.

SUMMARY

The present disclosure provides compositions and methods for generating hair cells and supporting cells by epigenetic modification of cochlear cells. Both cell division and cell differentiation are modified by changing epigenetic marks. The data presented herein show a role of Sox2-mediated and Wnt-mediated epigenetic modulation of the transcriptional regulation of Atoh1 and the effects of epigenetic modulation on expression of genes in the cell cycle and Notch and Wnt pathways.

Thus, in a first aspect the invention provides methods for treating sensorineural hearing loss associated with loss of auditory hair cells in a subject. The methods include administering to the subject, e.g., to the inner ear of the subject, a pharmaceutical composition comprising one or more of the following: a Histone Deacetylase (HDAC) inhibitor; a histone methyltransferase (HMT) inhibitor; a DNA methyltransferase (DNMT) inhibitor; a Histone Lysine Demethylase (KDM) inhibitor; an R-spondin; activators of c- and n-myc or Wnt agonists, and/or an inhibitory nucleic acid that specifically reduces expression of Hic1.

In another aspect, the invention provides the use fir the treatment of sensorineural hearing loss associated with loss of auditory hair cells in a subject of pharmaceutical compositions comprising one or more of the following: a Histone Deacetylase (HDAC) inhibitor; a histone methyltransferase (HMT) inhibitor; a DNA methyltransferase (DNMT) inhibitor; a Histone Lysine Demethylase (KDM) inhibitor; an R-spondin; activators of c- and n-myc or Wnt agonists, and/or an inhibitory nucleic acid that specifically reduces expression of Hic1.

In some embodiments, the HDAC inhibitor is selected from the group consisting of: Sodium Butyrate, Trichostatin A, hydroxamic acids, cyclic tetrapeptides, trapoxin B, depsipeptides, benzamides, electrophilic ketones, aliphatic acid compounds, pyroxamide, phenylbutyrate, valproic acid, hydroxamic acids, romidepsin, vorinostat (SAHA), belinostat (PXD101), LAQ824, panobinostat (LBH589), entinostat (MS275), CI-994 (N-acetyldinaline, also tacedinaline), Entinostat (SNDX-275; formerly MS-275), ENT-0334, SRT501, CUDC-101, JNJ-26481585, PC124781, Givinostat (ITF2357), and mocetinostat (MGCD0103).

In some embodiments, the EZH2/HMT inhibitor is selected from the group consisting of Deazaneplanocin A (DZNep), PR-SET7, GSK126, GSK EPZ005687; E7438; EI1; EPZ-6438; GSK343; BIX-01294, UNC0638, BRD4770, EPZ004777, AZ505 and PDB 4e47. In some embodiments, the EZH2/EMT inhibitor is selected from the group consisting of EPZ005687; E7438; EI1; EPZ-6438; GSK343; 01294, UNC0638, BRD4770, EPZ004777, AZ505 and PDB 4e47

In some embodiments, the DNMT inhibitor is selected from the group consisting of azacytidine, decitabine, Zebularine (1-(β-D-ribofuranosyl)-1,2-dihydropyrimidin-2-one), procainamide, procaine, (−)-epigallocatechin-3-gallate. MG98, hydralazine, RG108, and Chlorogenic acid.

In some embodiments, the KDM inhibitor is selected from the group consisting of tranylcypromine ((trans-2-phenylcyclopropyl-1-amine, trans-2-PCPA)) and analogs thereof with substitutions at the benzene ring; 2,4-pyridinedicarboxylic acid (2,4-PDCA); 5-Carboxy-8-hydroxyquinoline (IOX1) and n-octyl ester thereof. In some embodiments, the KDM inhibitor is selected from the group consisting of tranylcypromine ((trans-2-phenylcyclopropyl-1-amine, trans-2-PCPA)) and analogs thereof with substitutions at the benzene ring; 2,4-pyridinedicarboxylic acid (2,4-PDCA); 5-Carboxy-8-hydroxyquinoline (IOX1) n-octyl ester thereof, and Pargyline (N-Methyl-N-propargylbenzylamine).

In some embodiments, the R-spondin is human R-spondin 1 (hRSPO1), hRSPO2, hRSPO3, or hRSPO4.

In some embodiments, the inhibitory nucleic acid that specifically reduces expression of Hic1 is an siRNA, shRNA, or antisense oligonucleotide In some embodiments, the methods include administering the pharmaceutical composition to the subject, e.g., to the inner ear of the subject.

In some embodiments, the methods include application of the pharmaceutical composition to the round window membrane, e.g., intra-tympanic injection, or direct delivery into the inner ear fluids, e.g., using a microfluidic device.

In some embodiments, the pharmaceutical composition is formulated for administration to the inner ear of the subject, e.g., to the round window membrane, e.g., intra-tympanic injection, or direct delivery into the inner ear fluids, e.g., using a microfluidic device.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-1B (A) Cartoons showing the consensus binding sequence for Pax2 and Sox2 between positions 303-315 of the Atoh1 3' enhancer. Additional binding sites are shown as boxes. (B) Shown sequence homology between human Atoh1 (SEQ ID NO:2) and mouse Atoh1 (SEQ ID NO:1) within the binding region.

FIGS. 2A-D DNA gels resulting from chromatin immunoprecipitation (ChIP) studies using Pax2 or Sox2 antibodies. Chromatin-immunoprecipitation (ChIP) was performed with Pax2 or Sox2 antibodies (3 Mg each) in OC-1 cells, Protein complexes with sheared DNA bound to beads were resolved, and PCR was performed. Primers covering the entire length of the Atoh1 3' enhancer were used and the bands for the first 4 primers are shown. ChIP with a Pax2 antibody gives 2 bands between 4-375 by on the Atoh1 enhancer (the putative Sox2-Pax2 binding site lies between bases 303-335) and a faint band between 446-637 bp, apparently due to the second Pax2 binding site in the enhancer. ChIP with a Sox2 antibody with primer 153-375 yields one band (A). The region of DNA containing the binding site (153-375) is amplified by primers covering the proposed site after ChIP using Pax2 or Sox2 but not control (N IgG) antibodies in HEK cells transfected with the Atoh1 3' enhancer (B). Primer 4xP/S amplified the 4x-binding site construct after immunoprecipitation with Pax2 or Sox2 antibodies but not the serum control after CUP of OC-1 cells (input is 1:10 DNA before ChIP) transfected with the construct (C). Addition of siRNA for Pax2 or Sox2 (100 nM) reduced the amount of DNA precipitated by the Pax2 antibody from HEK cells (input is 1:10 DNA before ChIP) transfected with the 4x-binding site construct, Pax2, and Sox2 (D).

FIGS. 3A-C Schematic representation of the Atoh1 3' enhancer reporter constructs used for luciferase studies. Reporters contained either the intact mouse Atoh1 3' enhancer (A) or a 4x repeat of the Sox2-Pax2 binding site (B). The two imitated reporter constructs (C) based on the construct shown in b contained additional bases between the binding sites (Mutation 1) or had both binding sites mutated (Mutation 2).

FIGS. 4A-C Images of Western blots. Pax2 and Sox2 identified by IP and Western blotting of cell lysates. After transfection of OC-1 cells with Pax2 and Sox2, Western blotting for Sox2 was performed of the proteins obtained by IP of OC-1 cells with Pax2, Sox2 or control (N IgG) antibodies (A). IP of Pax2 and Sox2 transfected HEK cell lysates was followed by Western blotting for Sox2 or Pax2 (B). IP of HEK chromatin lysate with either Pax2 or Sox2 antibody was followed by Western blot analysis with either Sox2 or Pax2 antibody. Sox2 antibody precipitates Pax2, and Pax2 antibody precipitates Sox2 (C).

FIGS. 7A-B Bar graphs showing Atoh1 reporter activity in IEC6 cells transfected with 4x-binding site construct and 1 ng of Pax2 and Sox2 and treated with control siRNA or Pax2 and Sox2 siRNAs (100 nM total) show reduced activation (A). Overexpression of Pax2 (I ng) and Sox2 (0 ng 100 ng) in IEC6 cells transfected with the 4x-binding site construct (100 ng). Upregulation is greatest with a combination of 1 ng each Pax2 and Sox2 (B).

FIGS. 8A-8C (A) Schematic representation of the intact Atoh1 reporter construct used in the reporter assays summarized in (B) and (C). (B)-(C) Bar graphs showing Atoh1 reporter activity in HEK and Neuro2a cells transfected with Pax2, Sox2, or both Pax2 and Sox2.

DETAILED DESCRIPTION

Figure 5:
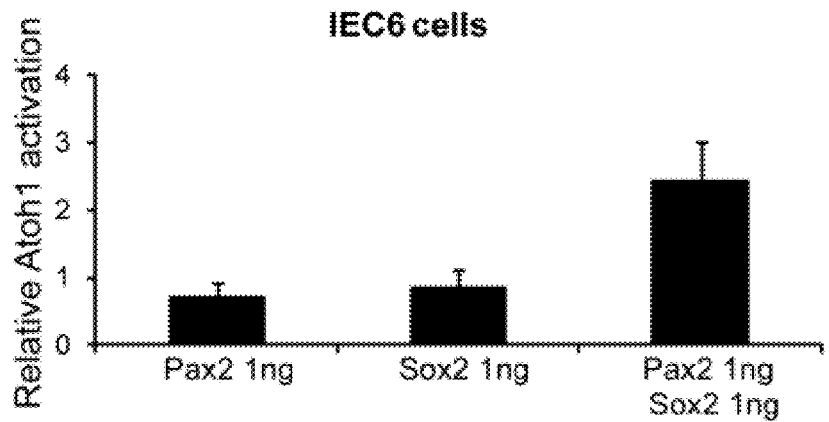
FIG. 5 Bar graph showing Atoh1 reporter activity in IEC6 cells in the presence of transfected Pax2. Sox2, or both Pax2 and Sox2.

The present disclosure is based, at least in part, on the surprising discovery that epigenetic modulation results in supporting cell division and increases Atoh1 expression, which is expected to increase generation of hair cells and support cells. As shown herein, Sox2 and Pax2 interact with each other and the three prime (3') enhancer for Atoh1, a transcription factor required for hair cell differentiation, at a compound consensus sequence, and these interactions lead to hair cell differentiation. Stimulation of the Wnt pathway also results in cell division and hair cell differentiation. In addition, modulating the epigenetic state of Atoh1 lead to an increase in Ato1 expression. As increased Ato1 leads to an increase in generation of hair cells, these epigenetic modifiers are expected to increase generation of hair cells from progenitors.

It is widely accepted that although cells capable of generating hair cells are present in the inner ear, natural hair cell regeneration in the inner ear is low (Li et al., Trends Mol. Med., 10, 309-315 (2004), Li et al., Nat. Med., 9, 1293-1299 (2003); Rask-Andersen et al., Hear. Res., 203, 180-191 (2005)). As a result, lost or damaged hair cells may not be adequately replaced by natural physiological processes (e.g., cell differentiation), and a loss of hair cells occurs. In many individuals, such hair cell loss can result in, e.g., sensorineural hearing loss, hearing impairment, and balance disorders. Therapeutic strategies that increase the number of hair cells in the inner ear will benefit a subject with hair cell loss, e.g., with one or more of these conditions.

In some embodiments, the present disclosure provides compositions and methods for preventing and/or treating auditory disease in a subject by increasing the number of sensory epithelial cells of the inner ear (e.g., hair cells and/or support cells), e.g., in the inner ear of the subject, by administering to the subject (e.g., to the inner ear of the subject) compositions that modulate the level of Sox2 and Pax2 in target cells. In other embodiments, the present disclosure provides compositions and methods for preventing and/or treating auditory disease in a subject by increasing the number of sensory epithelial cells of the inner ear (e.g., hair cells and/or support cells), e.g., in the inner ear of the subject, by administering to the subject (e.g., to the inner ear of the subject) compositions that modulate the level of β-catenin in target cells.

Atoh1 is important for specifying hair cell fate and its expression is tightly regulated (Kelly et al., Nat. Rev. Neurosci., 7:837-849 (2006)). Once activated, Atoh1 interacts with its 3' enhancer in a positive feedback loop to maintain expression (Helms et al., Development, 127: 1185-1196 (2000)). Despite the reported importance of Atoh1 for hair cell differentiation (Bermingham et al., Science, 284: 1837-1841 (1999); Zheng and Gao, Nat. Neurosci., 3:580-586 (2000); Izumikawa et al., Nat. Med., 11:271-276 (2005); Kelly et al., Nat. Rev. Neurosci., 7:837-849 (2006); Ciubbels et al., Nature, 455:537-541 (2008); Leon et al., J. Neurosci., 31:8351-8358 (2011)), pathways and factors involved in its regulation are reportedly poorly understood (Fritzsch et al., Dev. Dyn., 233:570-583 (2005)).

As described herein, targeted modulation of methylation can be used to regulate Atoh1 and promote hair cell differentiation.

Pax2/Sox2

Pax2 is a member of the paired box transcription factor family. The pax gene family encodes transcription factors implicated in the control of mammalian development and characterized by the presence of a 128 amino acid DNA-binding domain, referred to as the paired box Gruss and Walther, 69:719-722 (1992); Stuart et al., Ann. Rev. Gen., 28:219-236 91994)). In vertebrates, the nine members of the pax family can be classified in four groups based upon the presence of conserved structural domains, sequence homology and similar expression pattern (Dahl et al., Bioassays, 19:755-767 (1997); Mansuri. et al., J. Cell Sci., 18:35-42 (1994)). Pax2, Pax5 and Pax8 form group II, which is characterized by the presence of a paired domain, an octapeptide motif and a partial paired-class DNA-binding homeodomain. The pax gene family has been shown to play important roles in the development of various structures and organs (Zaiko et al., E. J. Endocrinol., 150:389-395 (2004). Absence of Pax2 results in major developmental defects of the central nervous system, eyes, ears and urogenital system (Favor et al., PNAS, 93:13870-13875 (1996)). Pax2 and its homologues are reportedly involved in the differentiation of the *Drosophila* shaft cells (Kavaler, Development, 126: 2261-72 (1999)), and in branching morphogenesis and nephron differentiation in the developing kidney (Narlis et al., J. Am. Soc. Nephrol., 18:1121-9 (2007)). Reports also support a role for Pax2 in inner ear development and hair cell differentiation (Warchol and Richardson, Dev. Neurobia, 69:191-202 (2009)). Mutations in Pax2 in humans result in renal coloboma characterized by kidney, eye, and ear abnormalities, including deafness (Schimmenti et al., Am. J. Hum. Genet., 60:869-878 (1997)). Pax2 hereafter refers to Pax2, DNA, MRNA, and protein.

Sox2 is an intronless gene that encodes a member of the SRY-related HMG-box (SOX) family of transcription factors involved in the regulation of embryonic development and in the determination of cell fate. The gene lies within an intron of another gene called SOX2 overlapping transcript (SOX2OT). Sox2 functions as a transcription factor that forms a trimeric complex with OCT4 on DNA and controls the expression of a number of genes involved in embryonic development such as YES1, FGF4, UTF1 and ZFP206 (see, e.g., Avilion et al., (2003); Masui et al., (2007); Takahashi et al., Cell, 131:861-872 (2007)). Sox2 is suggested to inhibit the expression of differentiation factors (Boyer et al., Cell, 122:947-956 (2005); Bylund et al., Nat. Neurosci., 6:1162-1168 (2003); Episkopou, Trends Neurosci., 28:219-221 (2005); Graham et al., Neuron, 39:749-765 (2003)), and to facilitate pluripotency of stem cells (Boyer et al., Cell, 122:947-956 (2005); Takahashi and Yamanaka, (2006); Yu et al., (2007)). Sox2 is one of four transcription factors known to reprogram various cell types to induced pluripotent stem cells (Yamanaka, Cell. Stem Cell, 1:39-49 (2007)).

In the sensory epithelia of the inner ear, Sox2 is initially expressed in progenitors of both hair cells and support cells (Kiernan et al., Nature, 434:1031-1035 (2005); Hume et al, Gene Expr. Patterns, 7:798-807 (2007); Neves et al., J. Comp. Neurobiol., 503:487-500 (2007)). Its expression is ultimately lost from hair cells after differentiation but is maintained in support cells (Kiernan et al., Nature, 434: 1031-1035 (2005); Hume et al, Gene Expr. Patterns, 7:798-807 (2007); Neves et at, J. Comp. Neurobiol., 503:487-500 (2007)). Mutations in Sox2 in humans result in eye defects that can be accompanied by deafness (Kelbernian et al., J. Clin. Invest., 116:2442-2455 (2006)). Roles for Sox2 in the development and/or regeneration of the inner ear are reported (see, e.g., Millima Ki et al., Dev. Biol. 338(2):262 (2010); Kiernan et al., Nature, 434:1031-1035 (2005). Sox2 expression was reported to reduce Ato11. expression and antagonize hair cell differentiation (Dabdoub et al., Proc. Natl. Acad. Sci., 105:18396-18401 (2008)). Other reports suggest a role for Sox2 in hair cell maintenance (Kiernan et al., Nature, 434:1031-1035 (2005)). Sox2 hereafter refers to Sox2, DNA, MBNA and protein.

Pax2 and Sox2 knockout animals have severe deficiencies in the developing inner ear (Burton et al., Dev, Biol. 272:

161-175 (2004); Lawoko-Kerali et al., J. Comp. Neurol., 442:378-391 (2002); Ohyama et al, Development, 133:865-875 (2006); Torres et al., Development 122:3381-3391 (1996)) and expression patterns of Sox2 and Pax2 in the inner ear are described in Moreno et al., PLoS One, 5(12): e15907 (2010).

Ezh2

As described herein, Sox2-Pax2 interact with each other and in association with other proteins recruit methyltransferases, and I3-catenin interacts with Tcf/Lef family proteins and with Hic-1, resulting in altered methylation and acetylation patterns at the Atoh1 enhancer. Sox2 and the Polycomb repressive complex 2 (PRC2) coregulate a number of genes in mammalian cells. Ezh2 (Enhancer of zeste homolog 2) protein is the enzymatic component of the PRC2, which represses gene expression by methylating lysine 27 of histone H3 (H3K27) (Qi et al., Proc Natl Acad Sci USA. 2012 Dec. 26; 109(5421360-5). Modulation of Ezh2 histone methyltransferase provides another pathway for increasing Atoh1 expression.

Modulation of the Epigenetic Status of Atoh1a

Generally speaking, epigenetic regulation of gene expression involves two major mechanisms. DNA methylation (i.e., at the CpG islands of gene promoters) and chromatin remodeling. The transition between transcriptionally silent heterochromatin to active euchromatin is thought to be controlled in part by proteins that add or remove modifications, e.g., acetylation or methylation, to histones, e.g., histone acetyltransferases (HATs); histone methyltransferases protein arginine methyltransferases (PRMTs) and histone lysine methyltransferases (HKMTs)); histone deacetylases (HDACs) and histone lysine demethylases (KDMs, the lysine-specific demethylases (LSD), and the Jumonji C (JmjC) families. See, e.g. Rotili and Mai, Genes & Cancer, 2011, 2(6):663-679.

The present disclosure provides that the epigenetic status of cochlear genes can be modulated to promote sensory epithelial cell proliferation and hair cell differentiation. Accordingly, the present disclosure provides compositions and methods for modulating cell number and Atoh1. levels in target cells to promote differentiation of the target cells towards or to a hair cell. These modifications can increase the activity of the Notch and Wnt pathways leading to proliferation of supporting cells. The proliferation can be due to increased expression of Wnt downstream targets such as cyclinD1, c-myc and n-myc. Epigenetic modification of cochlear genes can be achieved, e.g., by effecting an increase in H3K4 and a decrease in H3K9 and H3K27 methylation.

Thus, the methods described herein include the administration of compounds that modulate the epigenetic status of Atoh1. Such compounds include histone deacetylase (HDAC) inhibitors, DNA methyltransferases (DNMT) inihibitors, and Histone Methyl Transferase (HMT) inhibitors.

A number of HDAC inhibitors are known in the art, including but not limited to: Sodium Butyrate, Trichostatin A, hydroxamic acids, cyclic tetrapeptides, trapoxin B, depsipeptides, benzamides, electrophilic ketones, aliphatic acid compounds, pyroxamide, valproic acid, phenylbutyrate, valproic acid, hydroxamic acids, romidepsin; CI-994 (N-acetyldinaline, also tacedinaline); vorinostat (SAHA), belinostat (PXD101), LAQ824, panobinostat (LBH589), Entinostat (SNDX-275; formerly MS-275), EVP-0334, SRF501, CUDC-101, JNJ-26481585, PCI24781, Givinostat (ITF2357), and mocetinostat (MGCD0103).

A number of DNMT inhibitors are known in the art, including azacytidine, decitabine, Zebularine (1-(β-D-ribofuranosyl)-1,2-dihydropyrimidin-2-one), procainamide, procaine, (−)-epigallocatechin-3-gallate; MG98, hydralazine, RG108, and Chlorogenic acid. See also Gros et al., Biochimie. 2012 November; 94(11):2280-96.

A number of EZH2/HMT inhibitors are known in the art, including but not limited to: EPZ005687; E7438; E11 (Qi et al., 2012, supra); EPZ-6438; GSK343; BIX-01294, UNC0638; BRD4770, EPZ004777, AZ505 and PDB 4e47, and those described in Garapaly-Rao et al., Chem. Biol. 20(11):1329-1339 (2013); Ceccalth et al., ACS Chem Biol. 2013 Mar. 15; 8(3):543-8; US 20130303555; and WO2012/005805; see, e.g., Wagner and Jung, Nature Biotechnology 30:622-623(2012); and Yao et at, J Am Cheng Soc. 2011 Oct. 26; 133(42):16746-9, In some embodiments, inhibitors that act on the G9A H3K9 methyltransferase, are used. e.g., BIX-01294 or BRD4770.

Histone Lysine Demethylase (KDM) inhibitors can also be used, e.g., tranylcypromine ((trans-2-phenylcyclopropyl-1-amine; trans-2-PCPA)) and analogs thereof, e.g., with substitutions at the benzene ring, e.g., tranylcypromine 7, trans-2-PCPA analogue 28 (trans-2-pentafluorophenylcyclopropylamine, 2-PFPA), and trans-2-PCPA analogues carrying 4-bromo, 4-methoxy, and 4-trifluoromethoxy substitutions at the benzene ring (see, e.g., Gooden et al., Bioorg Med Chem Lett. 2008; 18(10):3047-51; Binda et al., J Am Chem Soc. 2010; 132(19):6827-33; Mimasu et al., Biochemistry. 2010; 49(30):6494-503; Benelkebir et al., Bioorg Med Chem. 2011; 19(12):3709-16; and Mimasu et al. Biochem Biophys Res Common. 2008; 366(1):15-22) or other inhibitors, e.g., 2,4-pyridinedicarboxylic acid (2,4-PDCA) (see, e.g., Kristensen et al., FEBS J. 2012 June; 279(11):1905-14), and inhibitors of jumonji C (jmjC)-containing KDMs, e.g., 5-Carboxy-8-hydroxyquinoline (IOX1) and n-octyl ester thereof; as described in Schiller et al., ChemMedChem, 2014 March; 9(3):566-71, or other inhibitors, as described in Spannhoff et al., ChemMedChem 2009; 4(10):1568-82; Varier and Timmers, Biochim Biophys Acta. 2011; 1815(1):75-89; Luo et al., J Am Chem Soc. Jun. 22; 2011; 133(24): 9451-9456; and Rotili et al., J Med Chem. 2014 Jan. 9; 57(1):42-55. Compositions can include one, two, or more compounds or agents that modulate the epigenetic status of cochlear genes, independently or otherwise. In addition, compositions can be adapted as pharmaceutical formulations.

Wat/Beta-Catenin, Hic1, and Lgr5

Wnt has been implicated in epigenetic control of gene expression, influencing the transcription of specific genes by altering the epigenetic structure of DNA, Enhanced Wnt/β-catenin signaling can drive Lgr5-positive cells present in the inner ear to act as hair cell progenitors (Shi et at, Proc Natl Acad Sci USA. Aug. 20, 2013; 110(34): 13851-13856), Beta-catenin acts by binding to members of the Tcf/Lef family for DNA binding (Tcf4 is active in the cochlea), which, like Sox2, also change the structure of DNA through an HMG domain (Brantjes et al., Biol Chem 383:255-261, 2002).

Hypermethylated in cancer 1 (Hic1), on chromosome 17p13.3, is frequently hypermethylated or deleted in human tumors. Evidence indicates that it is a tumor suppressor, as stable transfection in various cancer cell lines results in a significant decrease in their clonogenic survival. In addition to effects on direct binding to DNA promoter and enhancer regions, Hic1 sequesters Tcf-4 and beta-catenin, thereby preventing them from associating with the ICE-binding elements of the Wnt-responsive genes and reducing their effects on transcription. Hic1 overexpression suppresses TCF-mediated transcription. Hic1 RNAi has been shown to increase the basal expression and Wnt-responsiveness of the Axin2 gene, which is another Wnt target. See, e.g., Valenta et al., EMBO Journal (2006) 25, 2326-2337. The sequence 5'-(C)/(G)NG(C)/(G)GGGCA(C)/(A)CC-3' (SEQ ID NO:5) has been identified as optimal binding site sequence for Hic1, see Pinte et at, J Biol Chem. 2004 Sep. 10; 279(37): 38313-24.

As shown in Example 11, reducing Hic1 activ4, particularly in combination with increased beta-catenin, results in a dramatic increase in Atoh1 expression. Thus decreasing HIC1 activity provides another pathway for increasing Atoh1 expression.

Lgr5 is a co-receptor for Wnt signaling. Drugs that act as agonists or antagonists for the ligands of Lgr5, e.g., the R-sporadins, are also useful in the methods described herein, See, e.g., de Lau et al., Genome Biol. 2012; 13(3):242; US 20070059829; US 20050130145; U.S. Pat. No. 7,541,431.

Downstream targets of the Wnt pathway, such as c-myc and n-myc, are mediators of many of the effects of Witt signaling and are also useful targets for cochlear cell regeneration. Activators of c- and n-myc or Wnt agonists that increase the level of these proteins can therefore be used in the present methods as well, e.g., Wnt agonists (e.g., as described in Angew. Chem. Int Ed. 44, 1987-90, 2005 and WO2010/060088), and inhibitors of Wnt inhibitors, e.g., interfering RNA (siRNA, shRNA) directed against DIckopf, shisa, kremen, SOST sFRP, or axin.

Inhibition of Hic1 can be achieved by administration of an inhibitory nucleic acid that specifically reduces expression of Hic1, e.g., via RNA interference using an siRNA, shRNA, or antisense oligonucleotide. The sequence of human Hic1 is available in GenBank at Accession no. NM_006497.3 (hypermethylated in cancer 1 protein isoform 1) or NM_001098202.1 (hypermethylated in cancer 1 protein isoform 2, the longer isoform), and methods for making and delivering inhibitory nucleic acids that target a specific sequence are known in the art, see, e.g., Ramachandran and Ignacimuthu, Appl Biochem Biotechnol. 2013 March; 169 (6):1774-89; Li et al., J Control Release. 2013 Dec. 10; 172(2):589-600; Lochmatter and Mullis, Horm Res Paediatr. 2011; 75(1):63-9; Higuchi of al., BioDrugs. 2010 June; 24(3):195-205; and Ming et al., Expert Opin Drug Deliv. 2011 April; 8(4):435-49. The inhibitory nucleic acids can be DNA; RNA, DNA/RNA hybrids, or modified, e.g., as described in WO2012087983.

Pharmaceutical Formulations

The methods described herein include the manufacture and use of pharmaceutical compositions that include compounds identified herein, e.g., histone deacetylase (HIDAC) inhibitors and/or DNMT inhibitors and/or Ezh2 Histone Methyl Transferase (HMT) inhibitors, as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., dexamethasone; prednisone; gentamicin; brain-derived neurotrophic factor (BDNF); recombinant human insulin-like growth factor 1 (rhIGF-1), RIF (e.g., FGF2), and/or R-spondin; combinations of the active compounds disclosed herein can also be made and used. The present pharmaceutical compositions are formulated to be compatible with the intended route of administration.

In some embodiments, the compositions are delivered systemically, e.g., by parenteral, e.g., intravenous, intradermal, or subcutaneous administration.

In some embodiments, the compositions are administered by application to the round window membrane, e.g., application of a liquid or gel formulation to the round window membrane. Application to the round window membrane can be accomplished using methods known in the art, e.g., intra-tympanic injection of a liquid or gel formulation or by direct delivery into the inner ear fluids, e.g., using a microfluidic device.

In some embodiments, the compositions are delivered via a pump, e.g., a mini-osmotic pump, see, e.g., Takemura et al., Hear Res. 2004 October, 196(1-2):58-68, or a catheter, see, e.g., Charabi et al., Acta Otolaryngol Suppl. 2000; 543:108-10.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization, Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the therapeutic compounds are prepared with carriers that will protect the therapeutic compounds against rapid elimination from the body, such as a controlled release formulation, including implants and microencapsulated delivery systems. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, Nanoparticles, e.g., poly lactic/glycolic acid (PLGA) nanoparticles (see Tamura et al., Laryngoscope. 2005 November; 115(11):2000-5; Ge et al., Otolarynaol Head Neck Surg. 2007 October, 137(4):619-23; Horie et al., Laryngoscope. 2010 February; 120(2):377-83; Sakamoto et al., Acta Otolaryngol Suppl. 2010 November; (563):101-4) can also be used.

In some embodiments. the carrier comprises a polymer, e.g., a hydrogel, that increases retention of the compound on the round window and provides local and sustained release of the active ingredient. Such polymers and hydrogels are known in the art, see, e.g., Paulson et al., Laryngoscope. 2008 April; 118(4):706-11 (describing a chitosan-glycerophosphate (CGP)-hydrogel based drug delivery system); other carriers can include thermo-reversible triblock copolymer poloxamer 407 (see, e.g., Wang et al Audiol Neurootol. 2009; 14(6):393-401. Epub 2009 Nov. 16, and Wang et al., Laryngoscope. 2011 February; 121(2):385-91); poloxamer-based hydrogels such as the one used in OTO-104 (see, e.g., GB2459910; Wang et al., Audiol Neurotol 2009; 14:393-401; and Piu et al., Otol Neurotol. 2011 January; 32(1):171-9); Pluronic F-127 (see, e.g., Escobar-Chavez et al., J Pharm Pharm Sci. 2006; 9(3):339-5); Pluronic F68, F88, or F108; polyoxyethylene-polyoxypropylene triblock copolymer (e.g., a polymer composed of polyoxypropylene and polyoxyethylene, of general formula E106 P70 E106; see GB2459910, US20110319377 and US20100273864); MPEG-PCL diblock copolymers (Hyun et al., Biomacromolecules. 2007 April; 8(4):1093-100, Epub 2007 Feb. 28); hyaluronic acid hydrogels (Borden et al., Audiol Neurootol. 2011; 16(1):1-11); gelfoam cubes (see, e.g., Havenith et al., Hearing Research, February 2011; 272(1-2):168-177); and gelatin hydrogels (see, e.g., Inaoka et al., Acta Otolaryngol. 2009 April; 129(4):453-7); other biodegradable, biocompatible polymers can be used, such as ethylene vinyl acetate, poly anhydrides, polyglycolic acid, collagen, polyorthoesters, and polylactic acid. Tunable self-assembling hydrogels made from natural amino acids L and D can also be used, e.g., as described in Hauser et al e.g. Ac-LD6-COOH (L) e.g. Biotechnol Adv. 2012 May-June; 30(3):593-603. Such formulations can be prepared using standard techniques, or obtained commercially, e.g., from Alza Corporation and Nova Pharmaceuticals, Inc.

The pharmaceutical compositions can be included in a container, pack, or dispenser together with instructions for administration.

Methods of Treatment

The compounds and methods described herein are appropriate for the treatment of mammalian (e.g., human) subjects who have or are at risk of developing hearing disorders resulting from cochlear hair cell loss, preferably post-neonatal (e.g., child, adolescent or adult, e.g., above the age of 1, 2, 3, 4, 5, 6, 7, 8, 9, 10, 11, 12 or 13 years) subjects. The methods described herein can be used to treat cochlear hair cell loss and any disorder that arises as a consequence of hair cell loss in the ear, such as hearing impairments or deafness. These subjects can receive treatment with an agent described herein. The approach may be optimal for treatment of acute hearing loss shortly after the damage has occurred, and may be less effective after longer time periods when Notch signaling has returned to its baseline level in the adult.

In some instances, methods include selecting a subject. Subjects suitable for treatment include those at risk of hair cell loss or with hair cell loss and/or those at risk of sensorineural hearing loss or with sensorineural hearing loss. Any subject experiencing or at risk for developing hearing loss is a candidate for the treatment methods described herein. A human subject having or at risk for developing a hearing loss can hear less well than the average human being, or less well than a human before experiencing the hearing loss. For example, hearing can be diminished by at least 5, 10, 30, 50% or more.

The subject can have hearing loss associated with cochlear hair cell loss for any reason, or as a result of any type of event. For example, a subject can be deaf or hard-of-hearing as a result of a physical ototoxic insult, e.g., a traumatic event, such as a physical trauma to a structure of the ear. In preferred embodiments, the subject can have (or be at risk of developing) hearing loss as result of exposure to a sudden loud noise, or a prolonged exposure to loud noises. For example, prolonged or repeated exposures to concert venues, airport runways, and construction areas can cause inner ear damage and subsequent hearing loss; subjects who are subjected to high levels of environmental noise, e.g., in the home or workplace, can be treated using the methods described herein. A subject can have a hearing disorder that results from aging, e.g., presbycusis, which is generally associated with normal aging processes; see, e.g., Huang, Minn Med. 90(10):48-50 (2007) and Frisina, Annals of the New York Academy of Sciences, 1170: 708-717 (2009), and can occur in subjects as young as 18, but is generally more marked in older subjects, e.g., subjects over age 40, 45, 50, 55, 60, 65, 70, 75, 80, 85, or 90. A subject can have tinnitus (characterized by ringing in the ears) due to loss of hair cells. A subject can experience a chemical ototoxic insult, wherein ototoxins include therapeutic drugs including antineoplastic agents, salicylates, quinines, and aminoglycoside antibiotics, e.g., as described further below, contaminants in foods or medicinals, and environmental or industrial pollutants.

In some embodiments, the methods include administering to the subject a compound described herein within one, two, three, four, five, six, or seven days, or one, two, three, four, five, or six weeks of exposure to an ototoxic insult, e.g., a physical (noise, trauma) or chemical (ototoxin) insult that results in or could result in a loss of hair cells, and causes an increase in Notch signaling in the subject.

In some embodiments, a subject suitable for the treatment using the compounds and methods featured in the invention can include a subject having a vestibular dysfunction, including bilateral and unilateral vestibular dysfunction; the methods include administering a therapeutically effective amount of an agent described herein, e.g., by systemic administration or administration via the endolymphatic sac (ES). Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunctions that can be treated by the methods described herein can be the result of a genetic or congenital defect; an infection, such as a viral or bacterial infection; or an injury, such as a traumatic or nontraumatic injury, that results in a loss of vestibular hair cells. In some embodiments, balance disorders or Meniere's disease (idiopathic endolymphatic hydrops) may be treated by the methods described herein. Vestibular dysfunction is most commonly tested by measuring individual symptoms of the disorder (e.g., vertigo, nausea, and fuzzy vision).

Alternatively or in addition, the compounds and methods featured in the invention can be used prophylactically, such as to prevent, reduce or delay progression of hearing loss, deafness, or other auditory disorders associated with loss of hair cells. For example, a composition containing one or more compounds can be administered with (e.g., before, after or concurrently with) an ototoxic therapy, i.e., a therapeutic that has a risk of hair cell toxicity and thus a risk of causing a hearing disorder. Ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabutnetone, naproxen, oxaprozin, phenylbutazone, piroxicam, salsalate, sulindac, and tolmetin; diuretics; salicylates such as aspirin; and certain malaria treatments such as quinine and chloroquine. For example, a subject undergoing chemotherapy can be treated using the compounds and methods described herein. The chemotherapeutic agent cisplatin, for example, is known to cause hearing loss. Therefore, a composition containing one or more compounds can be administered with cisplatin therapy (e.g., before, after or concurrently with) to prevent or lessen the severity of the cisplatin side effect. Such a composition can be administered before, after and/or simultaneously with the second therapeutic agent. The two agents may be administered by different routes of administration.

In general, the compounds and methods described herein can be used to generate hair cell growth in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

In some instances, compositions can be administered to a subject, e.g., a subject identified as being in need of treatment, using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; transdermal routes of administration; and inhalation (e.g., nasal sprays).

In some instances, compositions can be administered to a subject, e.g., subject identified as being in need of treatment, using a systemic or local route of administration. Such local routes of administration include administering one or more compounds into the ear of a subject and/or the inner ear of a subject, for example, by injection and/or using a pump.

In some instances, compositions can be can be injected into the ear (e.g., auricular administration), such as into the luminae of the cochlea (e.g., the Scala media, Sc vestibulae, and Sc tympani). For example, compositions can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlea capsule. In another exemplary mode of administration, compositions can be administered in situ, via a catheter or pump. A catheter or pump can, for example, direct a pharmaceutical composition into the cochlea laminae or the round window of the ear. Exemplary drug delivery apparatus and methods suitable for administering one or more compounds into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a subject during a surgical procedure. In some embodiments, a catheter or pump can be positioned, e.g., in the ear (e.g., the outer, middle, and/or inner ear) of a subject without the need for a surgical procedure.

In some instances, compositions can be administered in combination with a mechanical device such as a cochlea implant or a hearing aid, which is worn in the outer ear. An exemplary cochlea implant that is suitable for use with the present invention is described by Edge et al., (U.S. Publication No. 2007/0093878).

In some instances, compositions can be administered according to any of the Food and Drug Administration approved methods, for example, as described in CDER Data Standards Manual, version number 004 (which is available at fda.give/cder/dsm/DRG/drg00301.htm).

In some instances, the present disclosure includes treating a subject by administering to the subject cells produced using the compositions and methods disclosed herein. in general, such methods can be used to promote complete or partial differentiation of a cell to or towards a mature cell type of the inner ear (e.g., a hair cell) in vitro. Cells resulting from such methods can then be transplanted or implanted into a subject in need of such treatment. Cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described herein. Target cells suitable for use in these methods are described above.

In some instances, methods can include administering one or more compositions disclosed herein and cells produced using the compositions and methods disclosed herein to a subject.

Administration of cells to a subject, whether alone or in combination with compounds or compositions disclosed herein, can include administration of undifferentiated, partially differentiated, and fully differentiated cells, including mixtures of undifferentiated, partially differentiated, and fully differentiated cells. As disclosed herein, less than fully differentiated cells can continue to differentiate into fully differentiated cells following administration to the subject.

Where appropriate, following treatment, the subject can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a subject can hear. Hearing tests in humans include behavioral observation audiometry (for infants to seven months), visual reinforcement orientation audiometry (for children 7 months to 3 years); play audiometry for children older than 3 years; and standard audiometric tests for older children and adults, e.g., whispered speech, pure tone audiometry; tuning fork tests; brain stem auditory evoked response (BAER) testing or auditory brain stein evoked potential (ABEP) testing. Oto-acoustic emission testing can be used to test the functioning of the cochlear hair cells, and electro-cochleography provides information about the functioning of the cochlea and the first part of the nerve pathway to the brain. In some embodiments, treatment can be continued with or without modification or can be stopped.

Dosage

An "effective amount" is an amount sufficient to effect beneficial or desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. In some embodiments, e.g., in subjects exposed to prolonged or repeated exposures to noise, e.g., normal noises such as are associated with activities of daily life (such as lawnmowers, trucks, motorcycles, airplanes, music (e.g., from personal listening devices), sporting events, etc.), or loud noises, e.g., at concert venues, airports, and construction areas, that can cause inner ear damage and subsequent hearing loss; e.g., subjects who are subjected to high levels of environmental noise, e.g., in the home or workplace, can be treated with repeated, e.g., periodic, doses of the pharmaceutical compositions, e.g., to prevent (reduce the risk of) or delay progression or hearing loss.

Dosage, toxicity and therapeutic efficacy of the therapeutic compounds can be determined by standard pharmaceutical procedures, e.g., in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. For example, samples of the perilymph or endolymph can be obtained to evaluate pharmacokinetics and approximate an effective dosage, e.g., in animal models, e.g., after administration to the round window. The dosage of such compounds lies preferably within a range of concentrations that include the ED50 with little or no toxicity. The dosage may vary within this range depending upon the dosage form employed and the route of administration utilized. For any compound used in the method of the invention, the therapeutically effective dose can be estimated from cell culture assays, and/or a dose may be formulated in animal models, alternatively, for those compounds that have been previously used in humans, clinically desirable concentrations can be used as a starting point. Such information can be used to more accurately determine useful doses in humans.

Kits

The compositions and/or cells disclosed herein can be provided in a kit. For example, kits can include (a) one or more compounds, such as in a composition that includes the compound, (b) cells that have been induced to differentiate, (c) informational material, and any combination of (a)-(c). The informational material can be descriptive, instructional, marketing or other material that relates to the methods described herein and/or to the use of the agent for the methods described herein. For example, the informational material relates to the use of the compound to treat a subject who has, or who is at risk for developing, a auditory hair cell loss hearing. The kits can also include paraphernalia for administering one or more compounds to a cell (in culture or in vivo) and/or for administering a cell to a patient, and any combination of the methods described herein.

In one embodiment, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In another embodiment, the informational material can include instructions to administer the pharmaceutical composition to a suitable subject, e.g., a human, e.g., a human having, or at risk for developing, auditory hair cell loss.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided. in any combination of formats.

In addition to the compound, the composition of the kit can include other ingredients, such as a solvent or buffer, a stabilizer, a preservative, a fragrance or other cosmetic ingredient, and/or a second agent for treating a condition or disorder described herein. Alternatively, the other ingredients can be included in the kit, but in different compositions or containers than the compound. In such embodiments, the kit can include instructions for admixing the agent and the other ingredients, or for using one or more compounds together with the other ingredients.

The kit can include one or more containers for the pharmaceutical composition. In some embodiments, the kit contains separate containers, dividers or compartments for the composition and informational material. For example, the composition can be contained in a battle (e.g., a dropper bottle, such as for administering drops into the ear), vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the pharmaceutical composition. For example, the kit can include a plurality of syringes, ampoules, foil packets, or blister packs, each containing a single unit dose of the pharmaceutical composition. The containers of the kits can be air tight and/or waterproof, and the containers can be labeled for a particular use. For example, a container can be labeled for use to treat a hearing disorder.

As noted above, the kits optionally include a device suitable for administration of the composition (e.g., a syringe, pipette, forceps, dropper (e.g., ear dropper), swab (e.g., a cotton swab or wooden swab), or any such delivery device).

EXAMPLES

The invention is further described in the following examples, which do not limit the scope of the invention described in the claims.

Example 1: Expression of Sox2 and Pax2 in Stem Cells Differentiating into Hair Cells As discussed above, Sox2 is an HMG domain transcription factor whose binding to DNA is enhanced and tissue-specific functions are conferred by partner interactions with a number of other transcription factors (Ambrosetti et al., Mol. Cell. Biol., 17:6321-6329 (1997); Karachi et al., Genes Dev., 15:1272-1286 (2001); Kondoh et al., Int. J. Dev. Biol., 48:819-827 (2004)). and Pax2 is a homeodomain transcription factor that binds to DNA through its paired domain. Both Pax2 and. Sox2 are expressed during development of the otocyst and are important for the development of the cochlea during tissue morphogenesis. Pax2 and Sox2 are both expressed in inner ear stem cells (Martinez-Monedero et al., Dev. Neurobiol., 68:669-684 (2008)). Their level of expression decreases when inner ear stein cells are transferred from a proliferative self-renewing culture (as floating neurospheres in growth factors) to a differentiating culture (as adherent cells in the absence of growth factors) (Martinez-Monedero et al., supra). The relationship between Sox2 and Pax 2 and the role of such relationship in the inner ear was investigated as described in the following examples.

Cellular expression profiles of Sox2 and Pax2 in stem cells differentiating into hair cells were reviewed using immunohistochemistry. Permeabilization and blocking was performed with blocking solution (0.3% Triton X-100, 15% heat inactivated goat or donkey serum in PBS) for 1 h. Diluted primary antibody (0.1% Triton X-100, and 10% heat inactivated goat or donkey serum in PBS) was applied overnight at 4° C. Antibody dilutions were: 1:100 for monoclonal mouse antibody against myosin Vila (Developmental Studies Hybridoma Bank), 1:100 for polyclonal rabbit antibody against Pax2 (Covance), and 1:300 for polyclonal goat antibody against Sox2 (Santa Cruz). Secondary antibodies (Alexafluor 488, 568, and 647-conjugated; Invitrogen) were used for detection of primary antibodies. Nuclei were visualized with 4,6-diamidino-2-phenylindole (Vector Laboratories). Staining was analyzed with epifluorescence microscopy (Axioskop2 Mot Axiocam, Zeiss) and confocal microscopy (TCD, Leica).

At day 3, differentiating cells exhibit patches of Pax2 and Sox2 expression with little overlap. At day 7, all cells that co-labelled for Sox2 and Pax2 showed robust expression of hair cell markers, Atoh1 or myosin VIIa. In a few cells, myosin VIIa positive cells were positive for Sox2 or Pax2, but not both. By day 10, most hair cell-like cells no longer expressed Pax2 or Sox2. About 30% of Atoh-1-positive cells co-expressed Pax2 and Sox2.

Example 2: Pax2 and Sox2 Co-Expression in Embryonic Hair Cell Progenitors

Expression of Pax2 and Sox2 was analyzed in vivo during development of mouse cochlea.

Embryos were collected at E12.5, 14.5, 15.5 and 17.5 (with identification of a positive plug in the morning counted as E0.5) and fixed in 4% paraformaldehyde for 4 hours at 4° C. After dehydration with sucrose (5% and 30%), embryos were embedded in OCT and kept at −80° C. For immunohistochemistry, tissue was cut (12 μm) and then stained as described in Example 1.

Expression of Pax2 and Sox2 was observed in the cochlea and vestibular system at the E12.5 time point. Furthermore, the observed expression pattern was segregated, with Pax2 seen on the abneural side of the cochlea and Sox2 on the neural side. A similar pattern was seen in the vestibular organs. Little overlap was observed in the ventromedial region and the future sensory epithelium.

At E14.5 in the cochlear duct, around the time of hair cell formation, only cells in the upper layer of the sensory epithelium, from which hair cells arise, showed overlapping expression for Pax2 and Sox2. At E15.5, Pas2-Sox2 co-expression was only seen in the area of maturing hair cells. At E17.5, hair cells continued to co-express Pax2 and Sox2 and showed strong myosin VIIa expression. These results in cochlear stem cells and in balance and hearing organs of the developing inner ear suggested that co-expression of these transcription factors occurs prior to the development of hair cells.

At P0, myosin VIIa-positive hair cells had lost most Sox2 expression, and Pax2 expression was lost in most inner hair cells. Developing supporting cells at all stages only stained for Sox2 and did not co-label for Pax2. in the vestibular system at E15.5, only developing myosin Vila-positive utricular and saccular hair cells showed co-labeling for Pax2 and Sox2. Despite broad expression in the developing otocyst, Pax2 and Sox2 were expressed in different regions of the cochlea and did not overlap except in cells that were destined to become hair cells.

Example 3: Interaction Between Pax2 and Sox2 and the Mold 3' Enhancer

The above-reported co-localization of Pax2 and Sox2 in hair cells during development and in new hair cells from inner ear stem cells suggested an important role for the transcription factors in the generation of hair cells. Since both transcription factors bind to DNA and act as transcriptional activators, a search was performed to identify consensus sequences, within the highly conserved murine and human Atoh1 3' enhancers, that may be sufficient to confer Pax2/Sox2-dependent heterologous Atoh1 expression in transgenic mice. This search identified a highly conserved site containing elements of adjacent Sox2 and Pax2 consensus sequences (see FIGS. 1A-B (boxes indicate additional binding sites for Pax2 and Sox2)). Consensus sites were separated by 2 bases.

To confirm that the above-identified putative binding sites are bound by Sox2 or Pax2, chromatin immunoprecipitation (ChIP) was performed in OC-1 cells, an inner ear cell line established from embryonic immorto-mouse cochlea that endogenously expresses many of the markers of outer hair cells, and shows robust expression of Atoh1 (Kalinec et al., Genes Dev., 15:1272-1286 (1999)). Endogenous levels of Pax2 and Sox2 levels are low in OC-1 cells, To address this, Pax2 and Sox2 cDNA was transfected.

For ChIP, 10 $CM^2$ culture dishes with OC-1 cells were seeded and transfected at 30% confluency using Lipofectamine (3 µl/µg DNA/nip and Pax2 or Sox2 cDNA (0.5 µg/ml. each) in Opti-MEM. After 48 h, cells were harvested and processed for ChIP. Chromatin was precipitated with either goat anti-Sox2 antibody (3 µg) or rabbit anti-Pax2 antibody (3 µg) or control non-immune goat serum or normal rabbit IgG (3 µg). Target DNA was amplified by PCR for Atoh1 regulatory regions using the primers shown in Table 1

TABLE 1

| Target (binding site) | Sense | Antisense |
|---|---|---|
| 4-193 | AAGGTCCGGCAATGAAGTTT (SEQ ID NO: 6) | AAAGGAACCAGTCAGCATGG (SEQ ID NO: 7) |
| 153-375 | CCATATGCCAGACCACTCCT (SEQ ID NO: 8) | GCGGTGTCCCAAAGAACTAA (SEQ ID NO: 9) |
| 352-512 | CGGGTTAGTTCTTTGGGACA (SEQ ID NO: 10) | GCTCCCCGTGAAATCAAATA (SEQ ID NO: 11) |
| 446-637 | GGTTTTGGCTCACCACACTT (SEQ ID NO: 12) | CTCTGGTCTCCTGCTGGTTC (SEQ ID NO: 13) |
| 570-815 | CGAATGGCACATCTACCAGA (SEQ ID NO: 14) | CGCGATCTTCACCTCTCAGT (SEQ ID NO: 15) |
| 808-968 | CGGGTTAGTTCTTTGGGACA (SEQ ID NO: 16) | GCTCCCCGTGAAATCAAATA (SEQ ID NO: 17) |
| 936-1108 | CTAGTGTCTCCCCAGGCAAG (SEQ ID NO: 18) | AAACTACCCCCACGCTTCTT (SEQ ID NO: 19) |
| 1089-1332 | AAGAAGCGTGGGGGTAGTTT (SEQ ID NO: 20) | AGCAAGGCTGTCTACGAGGA (SEQ ID NO: 21) |
| 1311-1493 | CCTCCTCGTAGACAGCCTTG (SEQ ID NO: 22) | TGGCTTAAGCATGCTCCTTT (SEQ ID NO: 23) |

Pax2 or Sox2 antibody was used to precipitate proteins bound to the DNA of OC-1 cells and PCR was performed for the entire enhancer.

For knockdown experiments, cells were transfected with siRNA (100 nM ON-TARGET plus, smart pool from Dharmacon for Pax2, Sox2, or non-targeting siRNA), using Gene Silencer (Genlantis) for 24 h according to the manufacturer's instructions. In addition, 2.5 µM DAPT was added during differentiation culture.

As shown in FIG. 2A, both Pax2 and Sox2 bound the DNA of the Atoh1. enhancer in the area of the putative binding site between bases 303-335. This indicated an active binding site for Pax2 and Sox2 on the Atoh1 3' enhancer. As shown in FIG. 2B, Pax2 and Sox2 antibodies, but not control antibodies, also precipitated DNA in the region of the binding site in HEK cells after transfection of Pax2 and Sox2 along with the Atoh1 3' enhancer construct represented in FIG. 3A. Antibodies for both Pax2 and Sox2 also precipitated a construct containing a 4×-repeat of the Pax2-Sox2 binding site from OC-1 cells (FIG. 2C and FIG. 3B).

After treatment with siRNA for Sox2 or Pax2, less DNA was precipitated with Pax2 antibody from HEK cells transfected with the 4×-binding site construct (FIG. 2D).

Example 4: Interaction Between Pax2 and Sox2

Direct protein-protein interaction between Pax2 and Sox2 was evaluated by immunoprecipitation (IP).

For transfection, OC-1 cells or spheres were seeded in DMEM/10% FBS at 40-50% confluency. Cells were transfected in optiMEM (GIBCO) with Pax2 or Sox2 cDNA or both (2 ng total for OC-1 cells, 20 ng total for spheres due to low transfection efficiency) and empty vector as a control. DNA was normalized to 2 ng or 20 ng total with empty vector. Transfection agent was Lipofectamine (3 µl/µg DNA/ml, Invitrogen). Transfection was stopped after 48 h, cells were harvested on ice and RNA was extracted immediately.

For immunoprecipitation, magnetic Dynabeads Protein G beads (Invitrogen) were incubated with 10 µg of either anti-Pax2 antibody or anti-Sox2 antibody or control normal goat or rabbit IgG at 4° C. overnight. Antibody supernatant was removed and beads were washed according to a Dynal IP Kit (Invitrogen). Beads were then incubated with cell lysate or chromatin lysate of HEK cells for 4 h at room temperature, followed by washing; protein was eluted with elution buffer and SDS sample buffer at 70° C. for 10 min. Elution product was loaded onto acrylamide gel and Western blot analysis was performed.

As shown in FIG. 4A, Pax2 antibody (and Sox2 as a control) precipitated Sox2 protein from OC-1 cells transfected with Pax2 and Sox2, while control IgG did not. Using cellular lysates of HEK cells transfected with Pax2 and Sox2, Pax2 antibody co-precipitated Sox2, and Sox2 antibody co-precipitated Pax2 (FIG. 4B), whereas neither Pax2 nor Sox2 were precipitated in the control. These data indicated that Sox2 and Pax2 interact directly. In addition, when nuclear lysate from HEK cells was used for IP, Sox2 antibody precipitated Pax2 and Pax2 antibody precipitated Sox2 (FIG. 4C). Thus, Pax2 and Sox2 were present in the complex and bound to DNA and to each other.

Example 5: The Pax2-Sox2 Consensus Sequence is Functionally Active

Enhancer activity was assessed via luciferase reporter assay in IEC6 cells. IEC6 cells were seeded onto 96-well plates 1 d before transfection. At 40-50% confluency, 100 ng of luciferase reporter construct (intact Atoh1 enhancer or 4×-binding site reporter or mutated contructs), 10 ng of Renilla luciferase construct and different amounts of Pax2 and Sox2 effector (from 0.1 ng-100 ng) were transfected with Lipofectamine (3 µl/µg DNA/ml) and incubated with the cells for 6 h. Two luciferase reporter constructs were transfected containing either the full-length Atoh1 3' enhancer or a 4×-repeat of the Pax2-Sox2 binding site (FIG. 3).

For RNAi, 100 nM total siRNA was transfected with GeneSilencer for 24 h. Cells were lysed after 48 h, and luciferase activity was measured using the Dual Luciferase Reporter Assay System (Promega) according to the manufacturer's instructions in a Wallac Victor2 1420 Multilabel Counter (Perkin-Elmer).

Figure 6:
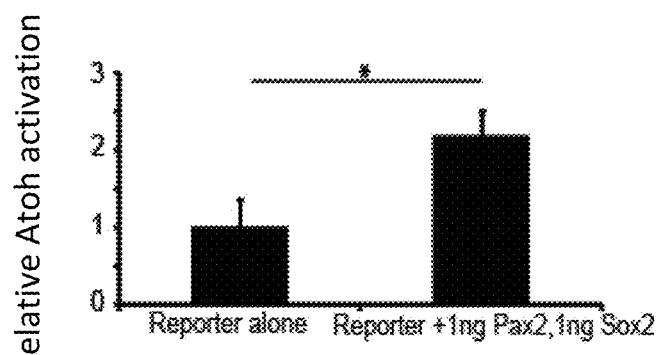
FIG. 6 Bar graph showing Atoh1 reporter activity in IEC6 cells. Luciferase activation of the 4x-binding site construct was assessed with or without exogenous transfection of Pax2 and Sox2 (1 ng each) in IEC6 cells. Activation is doubled by co-transfection of Pax2 and Sox2.

As shown in FIG. 5, transfection of Pax2 or Sox2 cDNA alone did not lead to significant activation of the Atoh1 3' enhancer. However, as shown in FIG. 5, right column, and FIG. 6, combination of equal amounts of Pax2 and Sox2 cDNA significantly increased activity. This increased activation with the single factors in the full-length enhancer could be due to individual sites for Pax and Sox proteins that could be bound at low affinity by Pax2 and Sox2.

Figure 7A:
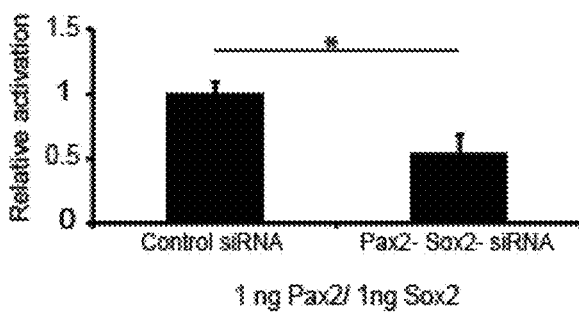

As shown in FIG. 7A, addition of siRNA for Pax2 and Sox2 after transfection of Pax2 and Sox2 cDNA (1 ng each) decreased activation of Atoh1. Activation of the Atoh1 enhancer was the greatest with low Pax2 and Sox2 concentrations (1 ng each) and high concentrations of Sox2 decreased activation of Atoh1 (FIG. 7B).

Similar experiments were conducted using a full-length Atoh1 3' enhancer (see FIG. 8A) in a neural cell line, Neuro2a, and HEK cells. As shown in FIGS. 8B-C, slight differences were seen in the concentrations of Pax2 and Sox2 needed for optimal activation, but similar for all cell lines. Only low concentrations of Pax2 and Sox2 activated the enhancer, and high concentrations of Sox2 abolished the effect.

Example 6: Characterization of the Pax2-Sox2 Binding Site for Atoh1 Activation Multiple mutations were introduced into the Pax2-Sox2 binding site for Atoh1 activation to further assess activity of the site.

In imitation 1, the spacing between the two binding sites was altered by the addition of 8 bases. Mutation 2 contained mutated Pax2 and Sox2 binding sites (see FIG. 3). Promoter activity was then assessed via reporter assay, conducted as described. above.

Figure 9A:
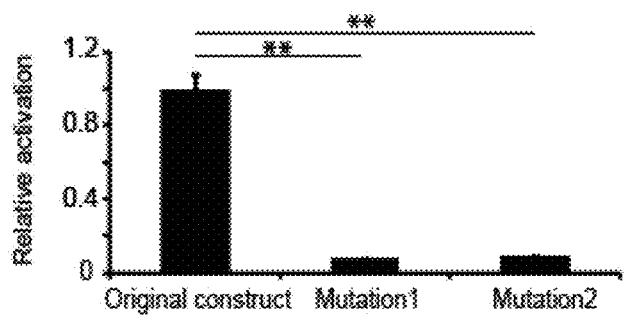
FIGS. 9A-D (A) Bar graph showing activity of mutant Atoh1 reporter constructs. (B) Schematic representation of the mutant Atoh1 reporter construct and its activity in IEC2 cells transfected with Sox2, Pax2, or both (B-D).
Figure 9B:
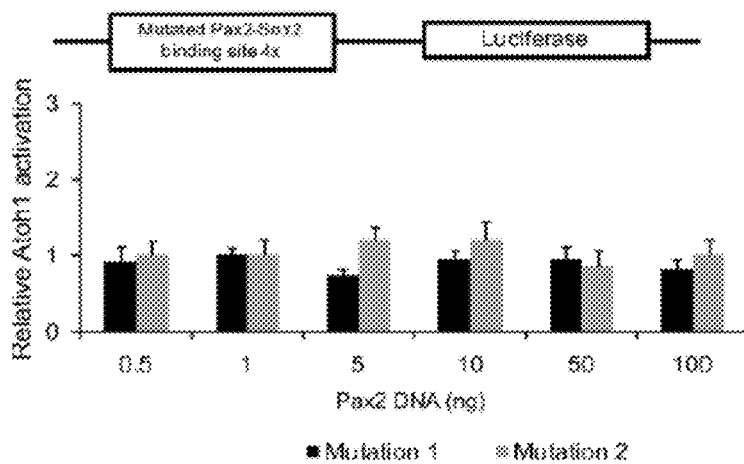
Figure 9C:
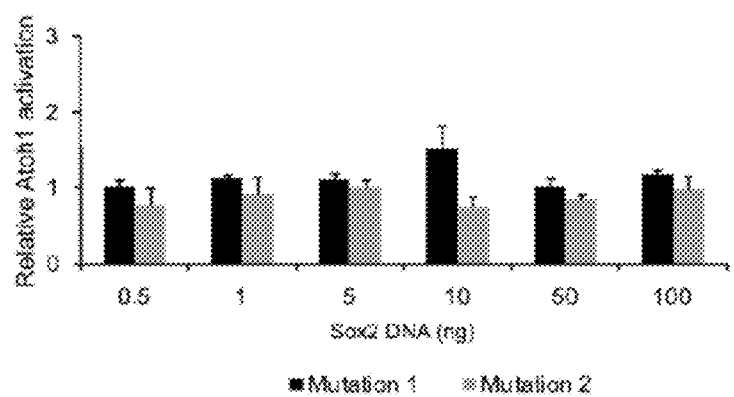
Figure 9D:
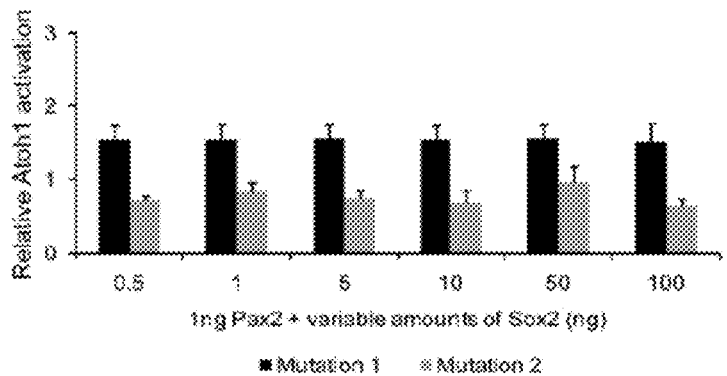

As shown in FIG. 9A, both mutation 1 and 2 significant reduced promoter activity and addition of Pax2 or Sox2 cDNA alone did not produce any activation in either mutated construct (FIGS. 9B and 9C). The promoter containing mutation 1 was activated when Pax2 and Sox2 were added together, but the promoter containing mutation 2 was not (FIG. 9D).

These data suggests that activation of the Atoh1 promoter requires interaction and binding of Pax2 or Sox2 to the Pax2 or Sox2 promoter binding site. In addition, activation required both Pax2 or Sox2 binding sites and maintenance of the wild-type spacing of the two sequences was critical for the protein-protein interaction.

Example 7: Levels of Pax2 and Sox2 Impact Promoter Activity

Figure 10:
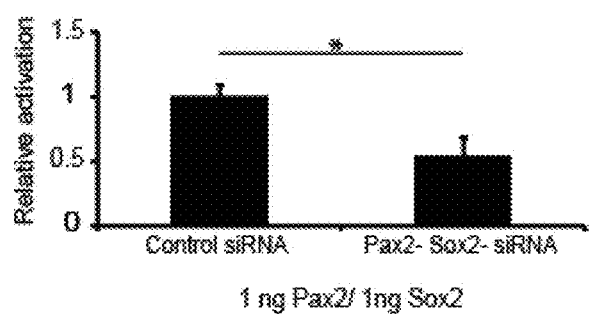
FIG. 10 Bar graph showing IEC6 cells transfected with 4x-binding site construct and 1 ng of Pax2 and Sox2 and treated with control siRNA or Pax2 and Sox2 siRNAs (100 nM total).

To confirm that levels of Pax2 or Sox2 affects activation of the enhancer RNAi was performed, siRNA against Sox2 and Pax2 was introduced into cells as described above. As shown in FIG. 10, after transfection of Pax2, promoter activity was reduced by 50%, compared to control siRNA, indicating a crucial role for Pax2 in activation of the binding site.

Atoh1 levels were measured in vitro in OC-1 cells or spheres by quantitative RT-PCR. For RT-PCR. total RNA was extracted from OC-1 cells or spheres treated with RAPT, FGF2, or DART and RNAi with the RiNeasy Maxi Kit (Qiagen) according to the manufacturer's instructions. RNA was denatured at 65° C. for 5 min. For reverse transcription, ImProm II (Promega) was used with random hexamers. Reverse transcription conditions were 25° C. for 5 min followed by 42° C. for 60 min. Reactions were terminated at 70° C. for 15 min. c: ANAs were mixed with Platinum quantitative PCR Supermix ROX with UDG (Invitrogen) and primers for Atoh1, Pax2 or Sox2 (ABI) according to the manufacturer's instructions. Gene expression was measured relative to 18S RNA. Samples were analyzed in 96 well plates in triplicate by quantitative PCR (Applied Biosystems 7900HT) using the following conditions: initial denaturation at 95° C. for 2 min, denaturation at 95° C. for 40 s and annealing/extension at 60' C for 35 s for 45 cycles.

Figures 11A, 11B:
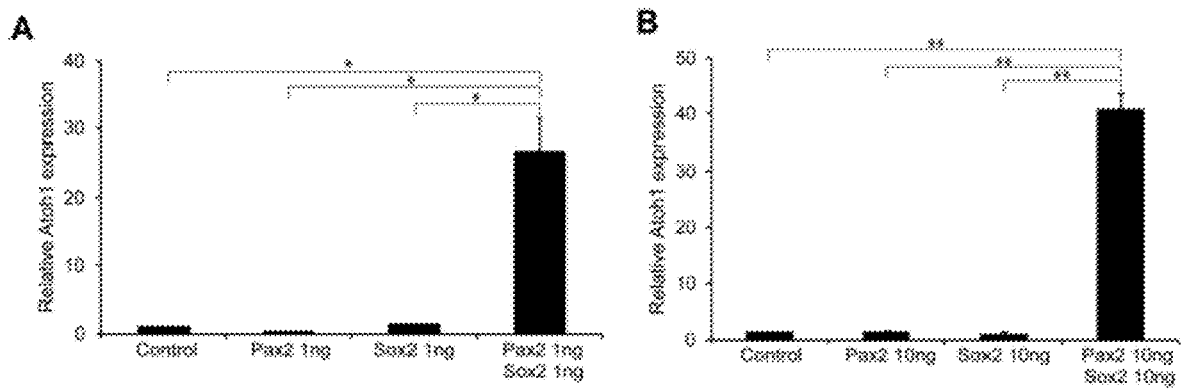
FIGS. 11A-B Bar graphs showing Atoh1 snRNA levels following transfection of Pax2, Sox2, or both.

As shown in FIG. 11, transfection with a combination of Pax2 and Sox2 led to a strong increase in Atoh1, whereas single transfection had no effect. Under stimulating conditions with DAPT, siRNA for Pax2 or Sox2 had little effect, but combined siRNAs for Pax2 and Sox2 significantly decreased Atoh1 as compared to control siRNA (relative ratio compared to control siRNA of 0.147±0.049 SEM, $p<0.001$ for OC-1 cells and 0427±0.132 SEM, $p<0.05$ for spheres).

Example 8: Increasing Differentiation of Hair Cells from Inner Ear Stem Cells using Pax2 and Sox2

To confirm that modulation of Pax2-Sox2 expression levels leads to the formation of hair cells, modulation of Pax2 and Sox2 expression was triggered in differentiating inner ear stem cells.

For each experiment, tissue of neonatal pups with C57BL/6 (Jackson Labs) or Atoh1-nGFP background were dissected on ice in HESS and the OC was harvested after removal of spiral ganglion neurons and stria vascularis as previously described (Parker et al., 2010).

Embryos were collected at E12.5, 14.5, 15.5 and 17.5 (with identification of a positive plug in the morning counted as E0.5) and fixed in 4% paraformaldehyde for 4 h at 4' C. After dehydration with sucrose (5% and 30%), embryos were embedded in OCT and kept al –80' C. For immunohistochemistry, tissue was cut (12 μm) and then stained as described for cultured cells.

For each experiment, cochleae of 4-6 neonatal C57BL/6 or Atoh1-nGFP pups (Lumpkin et al., Gene Expr. Patterns, 3:389-395 (2003)) that express GFP under the control of the Atoh1 enhancer (provided by Jane E. Johnson) were dissected in HBSS and the organ of Corti (OC) was separated from the stria vascularis and the spiral ganglion neurons. Tissues were dissociated in trypsin (0.25%) for 13 min in PBS at 37° C. 10% FBS in DMEM-high glucose medium was used to stop the reaction. After washing, tissue was manually dissociated. Titurated cells were then passed through a 70 μm cell strainer (BD Labware) to remove tissue debris. Single cells were cultured in DMEM-high glucose medium and F12 (1:1) supplemented with N2 and B27 (Invitrogen), and EGF (20 ng/mL; Chemicon), bFGF (10 ng/mL; Chemicon), IGF-1 (50 ng/mL; Chemicon), and heparan sulfate (50 ng/mL; Sigma). Single cells were maintained in ultra-low cluster plates (Costar) for several days in culture to obtain spheres14. For passage, spheres of the first generation were dissociated with a 25G needle and syringe (BD Lahware) 6-8 tunes. Single cell suspensions were cultured in fresh medium F12/DMEM (1:1) with the same growth factors to form spheres until use at the 4th to 5th generation.

In this example, modulation of Pax2 and Sox2 expression in the differentiating inner ear cells included reducing Sox2 expression levels while increasing Pax2 expression level. Sox2 expression was modulated using DAFT (Jeon et al., j. Neurosci., 31:8351-8358 (2011)). Pax2 expression was modulated using FGF2 (Adamska et al., Mech. Dev., 109: 303-313 (2001); Mansukhani et al., J. Cell. Biol., 168:1065-1076 (2005)). DAPT was used to decrease Sox2 and FGF2 to activate Pax2 expression in inner ear stein cells (see FIG. 12A). 4th-5th generation spheres or OC explants (P1-P2) were plated in 4-well plates (Greiner) on round 10 mm glass coverslips coated with poly-L-lysine (Cultrex) and attachment took place overnight in 10% FBS/DMEM-high glucose (GIBCO). Attachment was ensured with microscopic inspection and the medium was changed to serum-free DMEM-high glucose/F12 (mixed 1:1, GIBCO) and N2 and B27 (Invitrogen). Spheres were differentiated for 3, 7 or 10 d. For treatment, either DAFT (2.5 µM) or FGF (20 ng/ml) or control medium containing only DMSO (0.1%) were applied for 7d on spheres and 48 h on OC explants. Cells were harvested and further analyzed by immunohistochemistry. Axiovision 4.3 was used for data acquisition and the number of cells was quantified with Metamorph software. Cell counts were expressed as mean±standard deviation. An average of 1,000 cells were counted for spheres or 100 µm for OC explants. Origin software was used for statistical evaluation. Cell detection techniques are described in the Examples above.

Figure 12A:
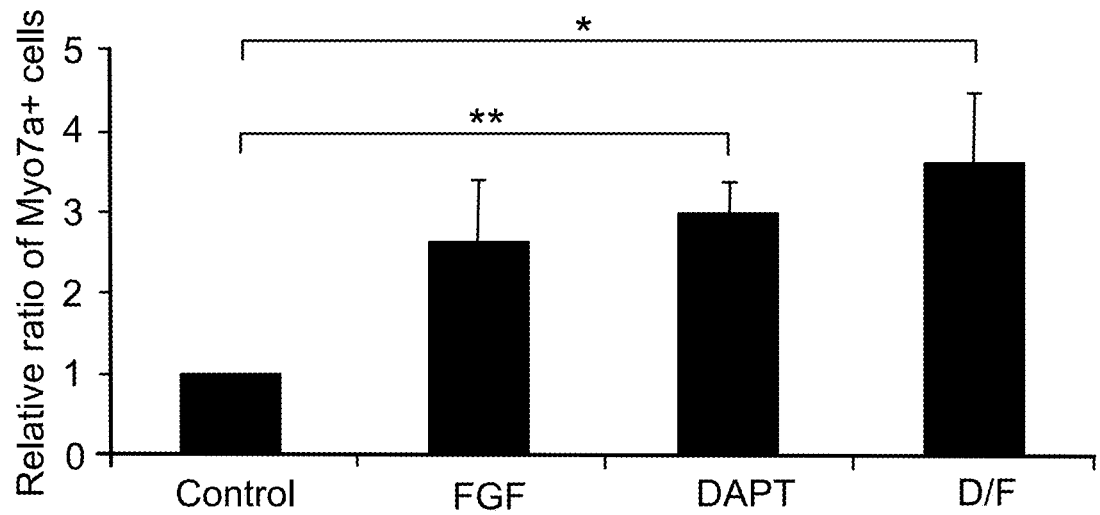
FIGS. 12A-B (A) Bar graph showing that the combination of FGF2 and DAPT results in the greatest increase in the number of myosin VIIa-positive cells as a fraction of the total cells compared to control (*, $p<0.05$; **, $p<0.01$). (B) Inner ear stem cells under differentiating conditions in the presence of DAPI and treated with siRNA for Pax2 or Sox2 or both (100 nM total) Counting myosin VIIa-positive cells vs. total number of cells showed a reduced number of hair cells. The greatest reduction (*, $p<0.05$; **, $p<0.01$) was found in cultures treated with a combination of siRNAs for Pax2 and Sox2 (50 nM each).
Figure 12B:
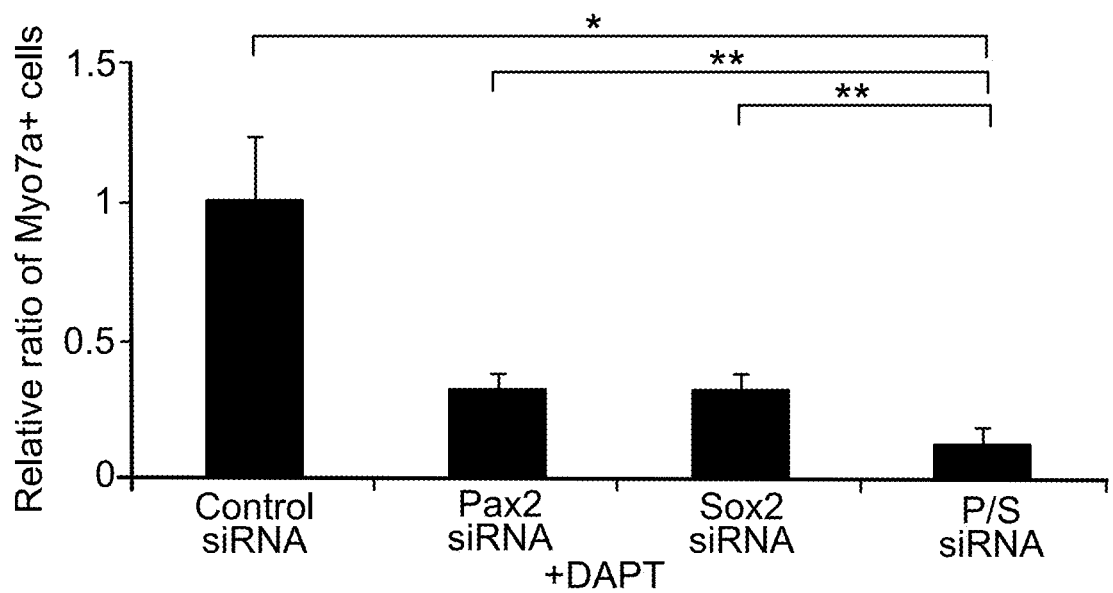

As shown in FIG. 12A, an increase in Atoh1-GFP or myosin VIIa positive cells was apparent after 7 d. The combination of FGF and DAFT produced the highest number of hair cell marker-positive cells (FIG. 12A). The number of Pax2 and Sox2 positive cells increased after FGF and DAPT treatment (from 29.52%±4.52% SEM of myosin VIIa-positive cells in control to 37.61%±4.28% SEM in treated spheres).

Figure 16A:
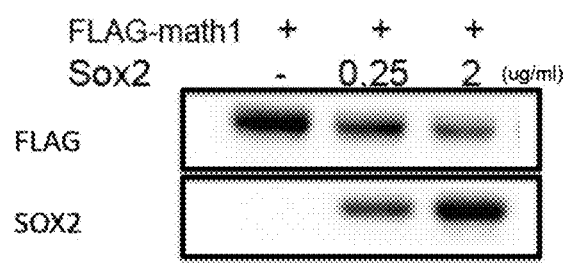
FIG. 16A Western blot of HEK cells co-transfected with FLAG-Atoh1 and Sox2 and probed after 24 hr with anti-FLAG (upper panel) and anti-Sox2 (lower panel) antibodies.
Figure 16B:
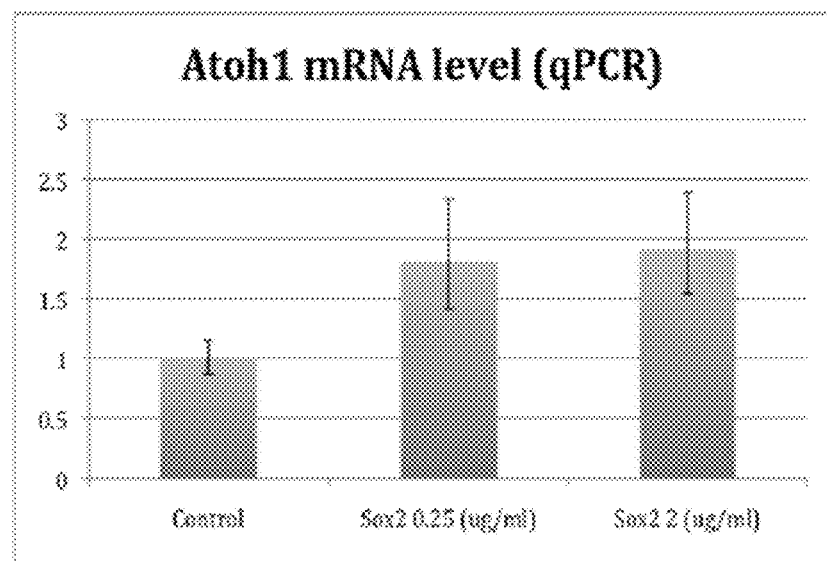
FIG. 16B Bar graph showing Atoh1 mRNA levels by real time qPCR in Sox2-transfected OC-1 cells.

To confirm that the increased differentiation was specifically caused by an effect of DAPT on Pax2 and Sox2, Pax2 and Sox2 expression was inhibited using siRNA (as described above) under stimulating conditions with DAPT. Hair cell number was analyzed at day 7 based on myosin Vila staining and Atoh1-GFP expression. As shown in FIG. 16B, siRNAs for Pax2 or Sox2 substantially decreased the number of hair cells, while control siRNA did not have an effect on the number of hair cells. As shown in FIG. 16B, the combination of siRNAs for Pax2 and Sox2 further decreased the number of hair cells, confirming that modulation of both Pax2 and Sox2 was needed for hair cell differentiation.

Example 9: Increasing Hair Cell Differentiation in the Organ of Corti

Postnatal hair cells in the organ of Corti have lost the ability to regenerate and are Pax2 and Sox2 negative. Previous data have shown that, when treated with DAPT, new hair cells form in the apical region of organ of Corti explants in culture (Doetzlhofer et al., Dev. Cell, 16:58-69 (2009); Yamamoto et al., J. Mol. Med., 84:37-45 (2006)). The impact of Pax2-Sox2 modulation of hair cell differentiation in the organ of Corti was assessed by contacting isolated organ of Corti with DAFT and/or FGF.

Samples were obtained and detected using methods described above. Organ of Corti explants (P1-P2) from Atoh1-GFP mice were contacted with DAPT, FGF2, or a combination of both for 48 h. Hair cell number was then assessed.

Figure 13A:
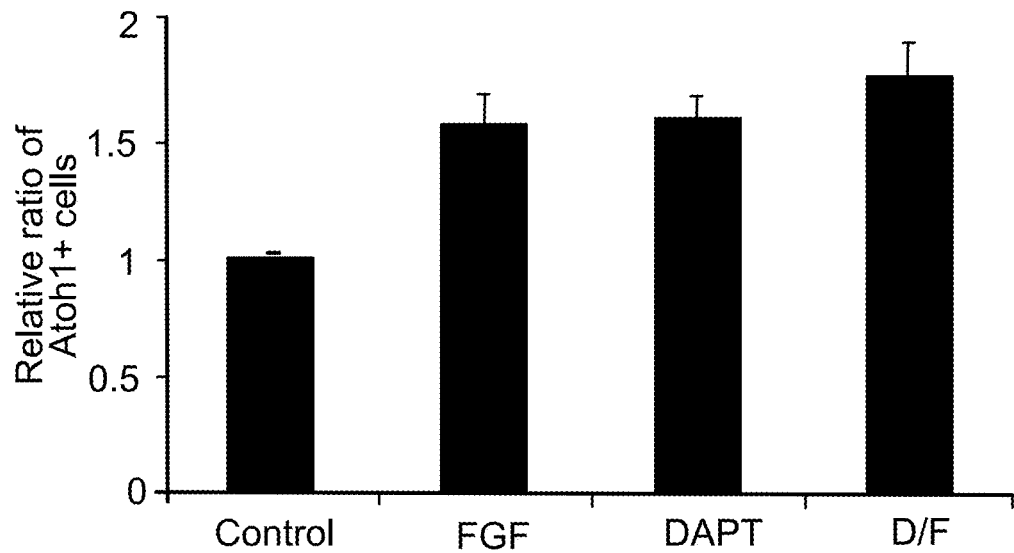
FIGS. 13A-B Treatment with DAPI and FGF2 results in the greatest increase in the percentage of Atoh1-GFP positive cells/100 μm (A) and in the percentage of Atoh1-GIP positive cells that co-express Pax2 and Sox2 (B).
Figure 13B:
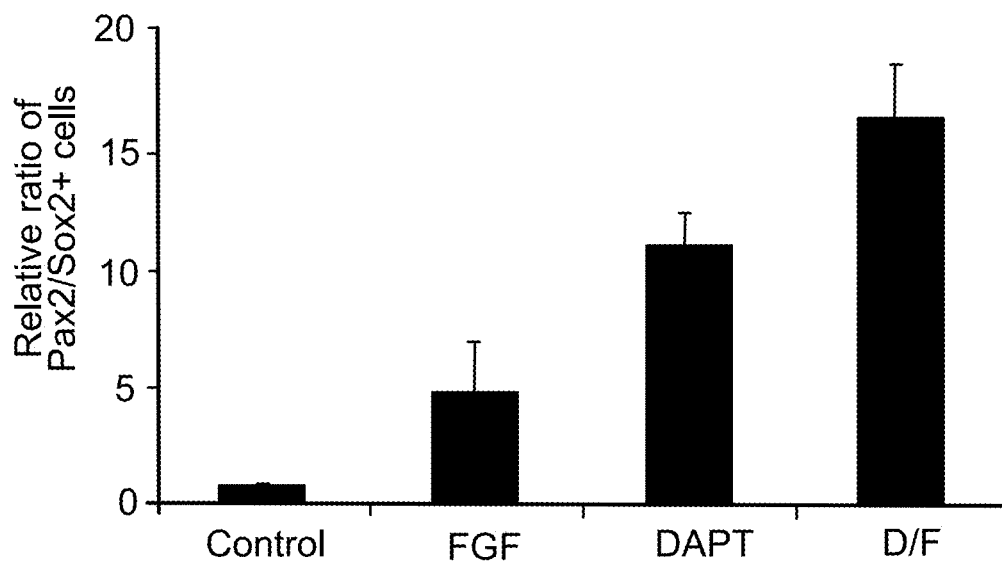

As shown in FIGS. 13A-B, no new hair cells were observed in the control, untreated, organ of Corti and any hair cells were Atoh1-GFP positive and Pax2 and Sox2 negative. In contrast, in both FGF2 and DAPT treated explants, additional outer hair cells were seen in the apex. Furthermore, the combination was the most effective at producing new hair cells (see FIG. 13A). In addition, the new hair cells co-expressed Pax2 and Sox2 (see FIG. 13B). Expression of Pax2 and Sox2 was lost at 72 h in culture. These data suggest that Pax2 was transiently upregulated in supporting cells, leading to Pax2-Sox2 activation of Atoh1, which resulted in direct transdifferentiation of supporting cells.

To confirm that DAPT had a direct effect on Pax2 and Sox2 regulation, postnatal organ of Corti explants were treated with siRNA for Pax2 and Sox2 under stimulating conditions with DAPT. Increased numbers of hair cells were observed after treatment with DAPT and control siRNA. In contrast, new hair cell formation was strongly inhibited by siRNAi for Pax2 or Sox2. These results underline the importance of Pax2 and Sox2 for activation of Atoh1 and regeneration of hair cells in the organ of Corti.

Example 10: Epigenetic Regulation of Atoh1

As described above in Examples 1-9, Sox2, a high-mobility group transcription factor, and Pax2, a paired homeodomain transcription factor, when co-expressed in inner ear stem cells always led to hair cell differentiation. In the developing otocyst, expression of Pax2 and Sox2 overlapped at the site of hair cell formation.

The finding that Sox2 bound to the Atoh1 enhancer led to the possibility of epigenetic regulation of Atoh1. Epigenetic regulation is suggested by the known role of Sox2 and Wnt signaling in stem cells (Kopp et al., 2008; Marson et al., 2008; Kim et al., 2009; Engelen et al., 2011). Sox2 directly alters DNA structure by binding to DNA through its HMG domain that inserts into the minor groove and bends the double helix (Engelen et al., 2011).

The effects of Sox2 are mediated by CHD7 in several organs, including the ear, by regulation of epigenetic signaling (Hurd et al., 2010; Engelen et al., 2011). The enzymatoc activity of CHD7 which binds to H3K4me sites, modifies chromatin to change the interaction of DNA with histones (Engelen et al., 2011). Its deficiency results in Charge syndrome, which has several severe manifestations, including deafness. The effects of Pax2 are mediated by its association with DNA binding protein, PTIP (Patel et al., 2007). PTIP has a known role in histone modifications through a direct association with H3 methyltransferase, KMT2a. PTIP together with Pax2 lead to a pattern of methylation characteristic of actively transcribed genes, an increase in H3K4 and a decrease in H3K9 and H3K27 methylation (Patel et al., 2007; Kim et al., 2009).

Cochlear expression of PTIP was assessed. Expression of CHD7 had been described, but PTIP was not known to be present in the cochlea. The P1 organ of Corn, where Sox2 and Pax2 pathways are active, showed strong expression of PTIP.

Figure 14A:
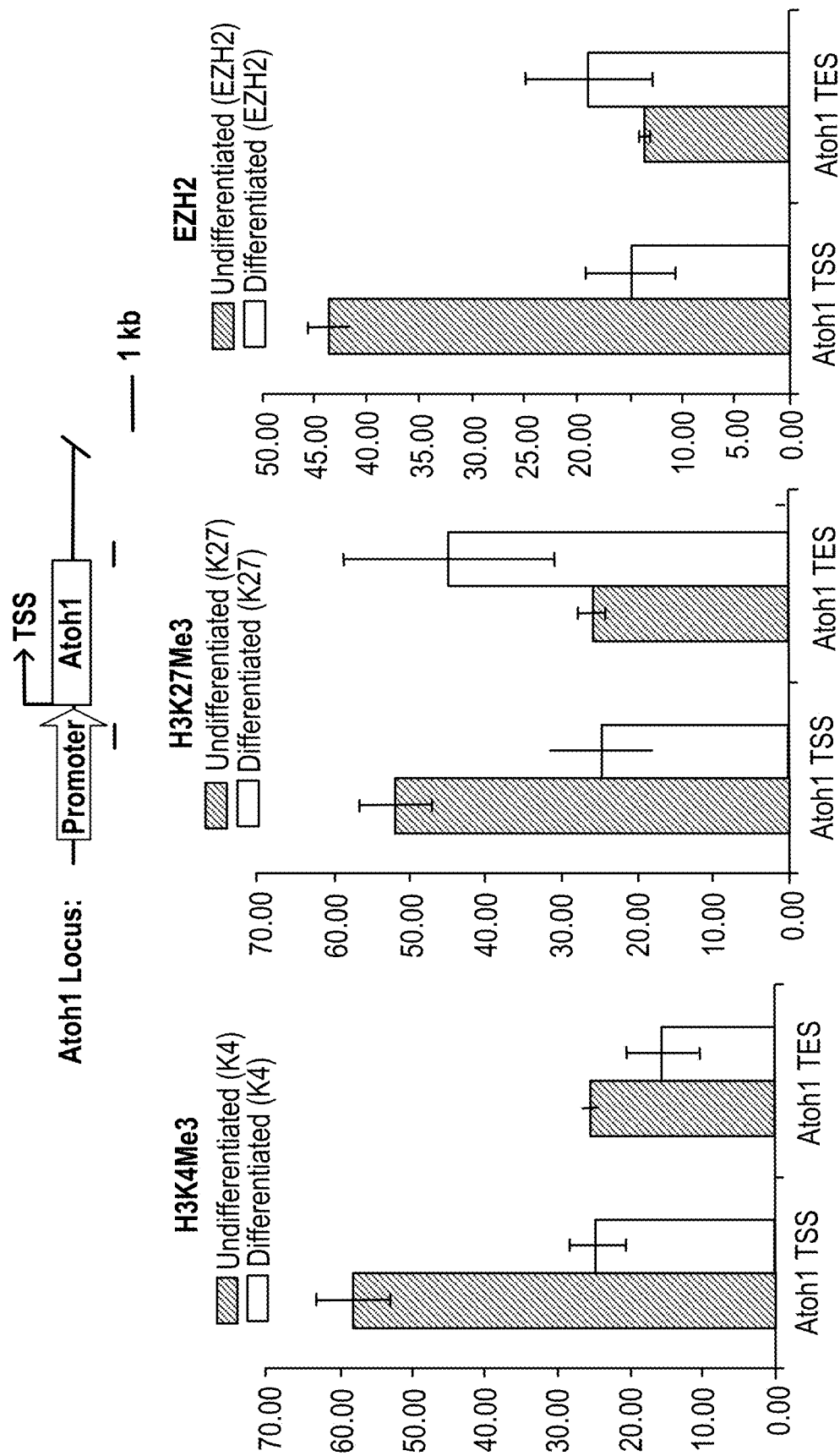
FIGS. 14A-B Bar graphs showing changes in relative levels of H3K4Me3, H3K27Me3 and EZH2 at the Atoh1 (14A) and Sox2 (14B) loci.
Figure 14B:
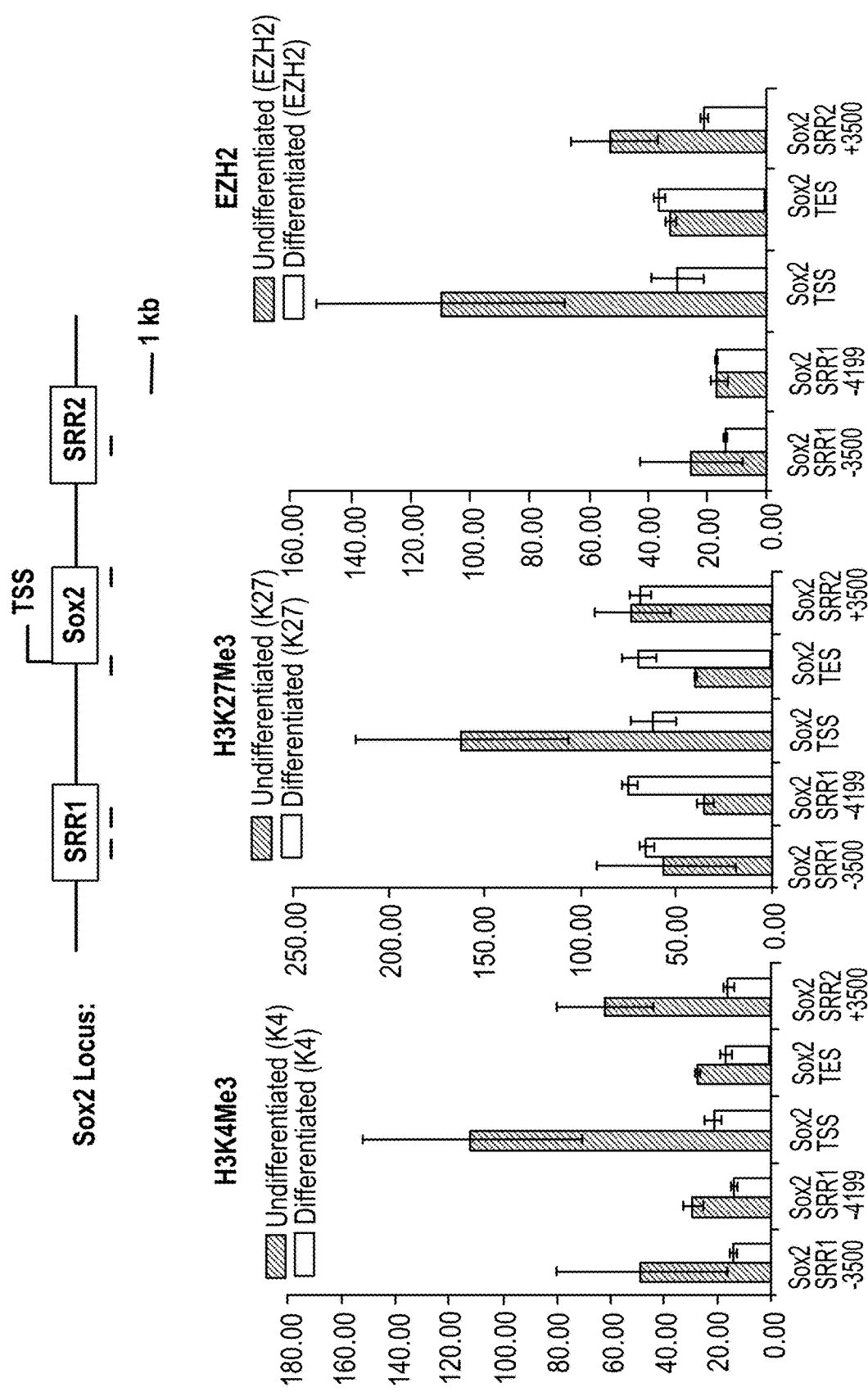

Changes in relative levels of H3K4Me3, H3K27Me3 and EZH2 at the Sox2 and Atoh1 loci were evaluated in undifferentiated and differentiated hair cell progenitor cell line, VOT-E36. Chromatin immunoprecipitation (ChIP) was performed using ActiveMotif© High Sensitivity protocol with antibodies to H3K4Me3, H31(27Me3, EZH2 and IgG (control). qPCR to regulatory regions of Atoh1 and Sox2 was performed using published primers (Bardot et al., 2013). Fold enrichment relative to IgG is presented in FIGS. 14A-B, Sox2 is a key stem cells gene also found in supporting cells in the inner ear. Atoh1 is a known Sox2 target, and Sox2 upregulates Atoh1 expression. Activating 1-13K4Me3 and inhibitory H3K27Me3 chromatin marks, along with EZH2 occupancy are altered with induced differentiation of VOT cells.

Figure 15:
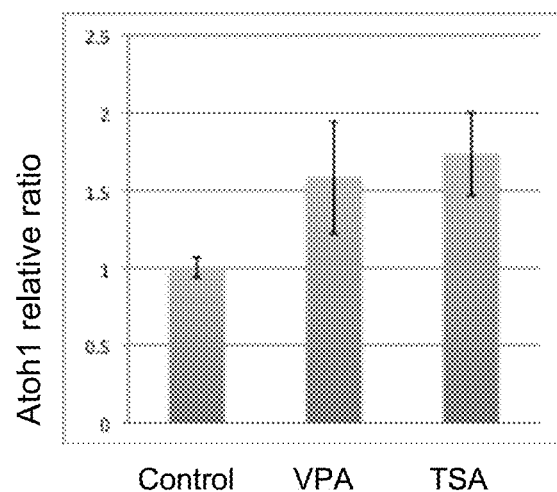
FIG. 15 Bar graph showing the effect of HDAC inhibitors on Atoh1. Treatment of OC-1 cells with HDAC inhibitors, VPA and TSA, increased expression of Atoh1, as measured by qRT-PCR. Values were calculated relative to 18S RNA.

One hypothesis was that Pax2-Sox2 binding to the Atoh1 enhancer resulted in increased expression of Atoh1 by an effect on the modification of histones. To address whether interaction with DNA-binding co-factors influenced bound histones at the Atoh1 locus, drugs that block histone modifications were used. As shown in FIG. 15, treatment of OC-1 cells with HDAC inhibitors both resulted in increased expression of Atoh1.

These results demonstrate that modification of the epigenetic state of Atoh1 can be used to upregulate expression of Atoh1, which is expected to lead to generation of new hair cells in vivo.

Example 11. Epigenetic Modulation of Atoh1 by Hoc1

Interactions of Sox2 and Wnt signaling pathways with the Atoh1 enhancer suggested the possibility that Sox2 and Wnt might act through epigenetic mechanisms. The present experiments test this hypothesis by determining the mechanisms through which Sox2, Pax2 and beta-catenin signaling affect the epigenetic status of DNA.

Beta-catenin activities are modulated by Hic1, which interacts with polycomb-like enzymes that methylate H3K27. Hic1 binds to and inactivates beta-catenin and Tcf4 (Valenta et al., EMBO J 25:2326-2337, 2006), and methylation of the Hic1 gene leads to overactivity of Atoh1 (Briggs et al, Cancer Res 68:8654-8656, 2008), which has been noted in tumors of the cerebellum (Briggs et al., Genes Dev 22:770-785, 2008; Boulay et al., J Biol Chem 287:10509-10524, 2012).

Cochlear expression of Hic1 was assessed. Hic1 expression was not known to be present in the cochlea. The P1 organ of Corti, where Sox2, Pax2 and beta-catenin pathways are active showed strong expression of Hic1.

Figure 17A:
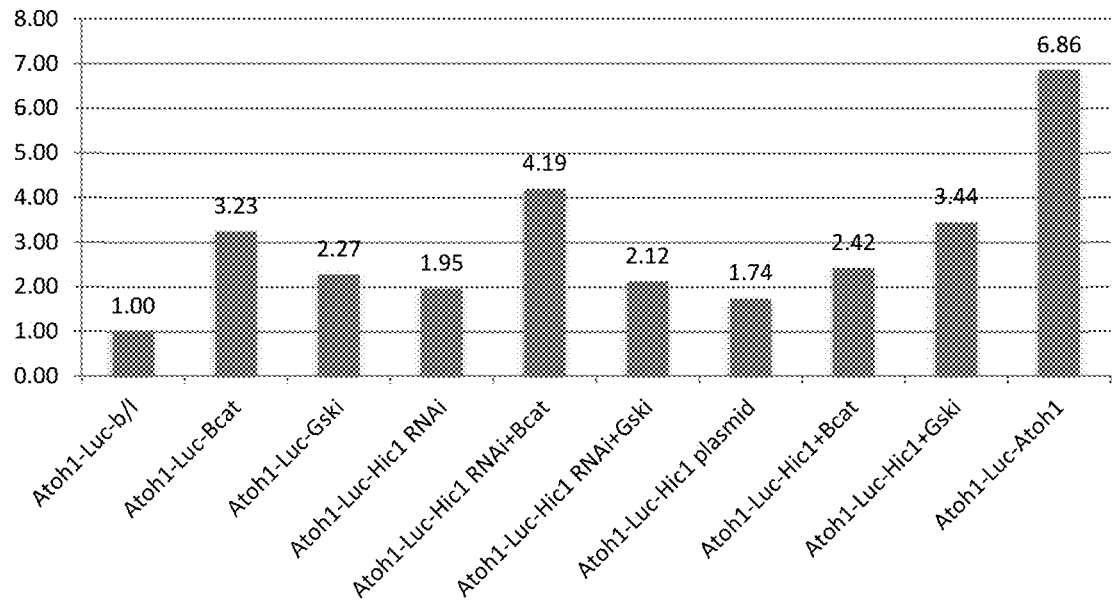
FIGS. 17A-B Bar graph showing Atoh1 mRNAmRN, levels in cells expressing various constructs as indicated.
Figure 17B:
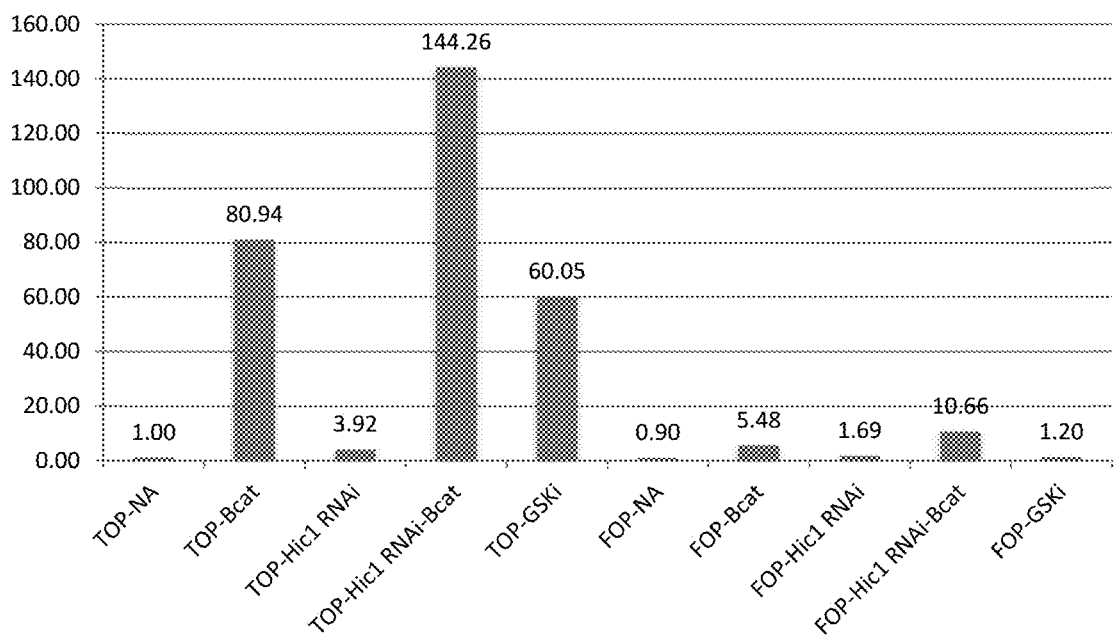

To address whether interaction with DNA-binding cofactors influence bound histones at the Atoh1 locus, inner ear stem cells were treated with Hic1 siRNA. As shown in FIGS. 17A-B, reducing Hid activity results in a dramatic increase in Atoh1 expression, and reducing Hic1 in combination with increased beta-catenin expression results in a synergistic increase in Atoh1 expression.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating sensorineural hearing loss associated with loss of auditory hair cells in a subject, the method comprising administering a therapeutically effective amount of a pharmaceutical composition comprising a DNA methyltransferase (DNMT) inhibitor to the inner ear of the subject.

2. The method of claim 1, wherein the DNMT inhibitor is selected from the group consisting of azacytidine, decitabine, Zebularine (1-(β-D-ribofuranosyl)-1,2-dihydropyrimidin-2-one), procainamide, procaine, (−)-epigallocatechin-3-gallate, MG98, hydralazine, RG108, and Chlorogenic acid.

3. The method of claim 1, comprising application of the pharmaceutical composition to the round window membrane.

4. The method of claim 3, wherein the pharmaceutical composition is applied via intra-tympanic injection or direct delivery into the inner ear fluids.

5. The method of claim 4, wherein the direct delivery into the inner ear fluids is applied using a microfluidic device.

6. The method of claim 1, wherein the pharmaceutical composition is formulated for administration to the inner ear of the subject.

7. The method of claim 1, wherein the pharmaceutical composition is formulated for administration to the round window membrane.

8. The method of claim 6, wherein the pharmaceutical composition is formulated for administration via intra-tympanic injection or direct delivery into the inner ear fluids.

9. The method of claim 8, wherein the pharmaceutical composition is formulated for administration via direct delivery into the inner ear fluids using a microfluidic device.

* * * * *

SEQUENCE LISTING

```
<160> NUMBER OF SEQ ID NOS: 23

<210> SEQ ID NO 1
<211> LENGTH: 35
<212> TYPE: DNA
<213> ORGANISM: Mus musculus

<400> SEQUENCE: 1
ccaaacaaac aaagagtcag cacttcttaa agtaa                              35

<210> SEQ ID NO 2
<211> LENGTH: 35
<212> TYPE: DNA
<213> ORGANISM: Homo sapiens

<400> SEQUENCE: 2
ccaaacaaac aaagaggcag catttcttaa agtaa                              35

<210> SEQ ID NO 3
<211> LENGTH: 43
<212> TYPE: DNA
<213> ORGANISM: Artificial Sequence
<220> FEATURE:
<223> OTHER INFORMATION: mutated binding site sequences

<400> SEQUENCE: 3
ccaaacaaac aaatgactga cgagtcagca cttcttaaag taa                     43

<210> SEQ ID NO 4
<211> LENGTH: 36
<212> TYPE: DNA
<213> ORGANISM: Artificial Sequence
<220> FEATURE:
<223> OTHER INFORMATION: mutated binding site sequences

<400> SEQUENCE: 4
```
ccaagtaaag taaagcttag gcacttctta aagtaa                                     36

<210> SEQ ID NO 5
<211> LENGTH: 12
<212> TYPE: DNA
<213> ORGANISM: Artificial Sequence
<220> FEATURE:
<223> OTHER INFORMATION: binding site sequence for Hic1
<220> FEATURE:
<221> NAME/KEY: misc_feature
<222> LOCATION: 2
<223> OTHER INFORMATION: n = A,T,C or G

<400> SEQUENCE: 5
sngsgggcam cc                                                               12

<210> SEQ ID NO 6
<211> LENGTH: 20
<212> TYPE: DNA
<213> ORGANISM: Artificial Sequence
<220> FEATURE:
<223> OTHER INFORMATION: synthetically generated primers

<400> SEQUENCE: 6
aaggtccggc aatgaagttt                                                       20

<210> SEQ ID NO 7
<211> LENGTH: 20
<212> TYPE: DNA
<213> ORGANISM: Artificial Sequence
<220> FEATURE:
<223> OTHER INFORMATION: synthetically generated primers

<400> SEQUENCE: 7
aaaggaacca gtcagcatgg                                                       20

<210> SEQ ID NO 8
<211> LENGTH: 20
<212> TYPE: DNA
<213> ORGANISM: Artificial Sequence
<220> FEATURE:
<223> OTHER INFORMATION: synthetically generated primers

<400> SEQUENCE: 8
ccatatgcca gaccactcct                                                       20

<210> SEQ ID NO 9
<211> LENGTH: 20
<212> TYPE: DNA
<213> ORGANISM: Artificial Sequence
<220> FEATURE:
<223> OTHER INFORMATION: synthetically generated primers

<400> SEQUENCE: 9
gcggtgtccc aaagaactaa                                                       20

<210> SEQ ID NO 10
<211> LENGTH: 20
<212> TYPE: DNA
<213> ORGANISM: Artificial Sequence
<220> FEATURE:
<223> OTHER INFORMATION: synthetically generated primers

<400> SEQUENCE: 10
cgggttagtt ctttgggaca                                                       20

```
<210> SEQ ID NO 11
<211> LENGTH: 20
<212> TYPE: DNA
<213> ORGANISM: Artificial Sequence
<220> FEATURE:
<223> OTHER INFORMATION: synthetically generated primers

<400> SEQUENCE: 11
gctccccgtg aaatcaaata                                              20

<210> SEQ ID NO 12
<211> LENGTH: 20
<212> TYPE: DNA
<213> ORGANISM: Artificial Sequence
<220> FEATURE:
<223> OTHER INFORMATION: synthetically generated primers

<400> SEQUENCE: 12
ggttttggct caccacactt                                              20

<210> SEQ ID NO 13
<211> LENGTH: 20
<212> TYPE: DNA
<213> ORGANISM: Artificial Sequence
<220> FEATURE:
<223> OTHER INFORMATION: synthetically generated primers

<400> SEQUENCE: 13
ctctggtctc ctgctggttc                                              20

<210> SEQ ID NO 14
<211> LENGTH: 20
<212> TYPE: DNA
<213> ORGANISM: Artificial Sequence
<220> FEATURE:
<223> OTHER INFORMATION: synthetically generated primers

<400> SEQUENCE: 14
cgaatggcac atctaccaga                                              20

<210> SEQ ID NO 15
<211> LENGTH: 20
<212> TYPE: DNA
<213> ORGANISM: Artificial Sequence
<220> FEATURE:
<223> OTHER INFORMATION: synthetically generated primers

<400> SEQUENCE: 15
cgcgatcttc acctctcagt                                              20

<210> SEQ ID NO 16
<211> LENGTH: 20
<212> TYPE: DNA
<213> ORGANISM: Artificial Sequence
<220> FEATURE:
<223> OTHER INFORMATION: synthetically generated primers

<400> SEQUENCE: 16
cgggttagtt ctttgggaca                                              20

<210> SEQ ID NO 17
<211> LENGTH: 20
<212> TYPE: DNA
<213> ORGANISM: Artificial Sequence
<220> FEATURE:
<223> OTHER INFORMATION: synthetically generated primers
```

```
<400> SEQUENCE: 17
gctccccgtg aaatcaaata                                              20

<210> SEQ ID NO 18
<211> LENGTH: 20
<212> TYPE: DNA
<213> ORGANISM: Artificial Sequence
<220> FEATURE:
<223> OTHER INFORMATION: synthetically generated primers

<400> SEQUENCE: 18
ctagtgtctc cccaggcaag                                              20

<210> SEQ ID NO 19
<211> LENGTH: 20
<212> TYPE: DNA
<213> ORGANISM: Artificial Sequence
<220> FEATURE:
<223> OTHER INFORMATION: synthetically generated primers

<400> SEQUENCE: 19
aaactacccc cacgcttctt                                              20

<210> SEQ ID NO 20
<211> LENGTH: 20
<212> TYPE: DNA
<213> ORGANISM: Artificial Sequence
<220> FEATURE:
<223> OTHER INFORMATION: synthetically generated primers

<400> SEQUENCE: 20
aagaagcgtg ggggtagttt                                              20

<210> SEQ ID NO 21
<211> LENGTH: 20
<212> TYPE: DNA
<213> ORGANISM: Artificial Sequence
<220> FEATURE:
<223> OTHER INFORMATION: synthetically generated primers

<400> SEQUENCE: 21
agcaaggctg tctacgagga                                              20

<210> SEQ ID NO 22
<211> LENGTH: 20
<212> TYPE: DNA
<213> ORGANISM: Artificial Sequence
<220> FEATURE:
<223> OTHER INFORMATION: synthetically generated primers

<400> SEQUENCE: 22
cctcctcgta gacagccttg                                              20

<210> SEQ ID NO 23
<211> LENGTH: 20
<212> TYPE: DNA
<213> ORGANISM: Artificial Sequence
<220> FEATURE:
<223> OTHER INFORMATION: synthetically generated primers

<400> SEQUENCE: 23
tggcttaagc atgctccttt                                              20
```